United States Patent
Potkay

(10) Patent No.: US 12,296,080 B2
(45) Date of Patent: May 13, 2025

(54) MICROFLUIDIC DIFFUSION DEVICES AND SYSTEMS, AND METHODS OF MANUFACTURING AND USING SAME

(71) Applicant: United States Government as Represented by the Department of Veterans Affairs, Washington, DC (US)

(72) Inventor: Joseph A. Potkay, Ann Arbor, MI (US)

(73) Assignee: United States Government as Represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 17/984,408

(22) Filed: Nov. 10, 2022

(65) Prior Publication Data
US 2023/0084914 A1    Mar. 16, 2023

Related U.S. Application Data

(62) Division of application No. 16/499,999, filed as application No. PCT/US2018/025952 on Apr. 3, 2018, now Pat. No. 11,759,558.
(Continued)

(51) Int. Cl.
*A61M 1/16*        (2006.01)
*A61M 1/36*        (2006.01)
(Continued)

(52) U.S. Cl.
CPC ........ *A61M 1/1698* (2013.01); *A61M 1/1623* (2014.02); *A61M 1/3666* (2013.01);
(Continued)

(58) Field of Classification Search
CPC .... A61M 1/00; A61M 1/1698; A61M 1/1623; A61M 1/3666; A61M 2205/0244;
(Continued)

(56) References Cited

U.S. PATENT DOCUMENTS

| | | | |
|---|---|---|---|
| 3,892,533 A | 7/1975 | Freedman et al. | |
| 5,192,320 A | 3/1993 | Anazawa et al. | |

(Continued)

FOREIGN PATENT DOCUMENTS

| | | |
|---|---|---|
| EP | 1941919 A1 | 7/2008 |
| FR | 2445163 A1 | 7/1980 |
| WO | 2011150216 A1 | 12/2011 |

OTHER PUBLICATIONS

Potkay, Ph.D., J.A.; A High Efficiency Micromachined Artificial Lung; Transducers 2009; Jun. 21-25, 2009; Downloaded on Dec. 20, 2021; pp. 2234-2237.

(Continued)

*Primary Examiner* — John Kim
(74) *Attorney, Agent, or Firm* — Ballard Spahr LLP

(57) ABSTRACT

Disclosed herein are rolled-membrane microfluidic diffusion devices and corresponding methods of manufacture. Also disclosed herein are three-dimensionally printed microfluidic devices and corresponding methods of manufacture. Optionally, the disclosed microfluidic devices can function as artificial lung devices.

20 Claims, 15 Drawing Sheets

Related U.S. Application Data

(60) Provisional application No. 62/480,809, filed on Apr. 3, 2017.

(51) Int. Cl.
*B01D 63/00* (2006.01)
*B01D 63/06* (2006.01)
*B01D 67/00* (2006.01)
*B01D 69/02* (2006.01)
*B01D 69/04* (2006.01)
*B01D 69/12* (2006.01)
*B01D 71/70* (2006.01)

(52) U.S. Cl.
CPC ......... *B01D 63/005* (2013.01); *B01D 63/065* (2013.01); *B01D 67/00045* (2022.08); *B01D 67/0032* (2013.01); *B01D 67/009* (2013.01); *B01D 69/02* (2013.01); *B01D 69/04* (2013.01); *B01D 69/1213* (2022.08); *B01D 71/701* (2022.08); *A61M 2205/0244* (2013.01); *A61M 2205/8206* (2013.01); *A61M 2207/00* (2013.01); *A61M 2209/088* (2013.01); *B01D 2325/04* (2013.01); *B01D 2325/08* (2013.01)

(58) Field of Classification Search
CPC ...... A61M 2205/8206; A61M 2207/00; A61M 2209/088; B01D 63/005; B01D 63/065; B01D 69/02; B01D 69/04; B01D 69/12; B01D 69/1213; B01D 71/70; B01D 71/701; B01D 2325/04; B01D 2325/08; B01D 67/0004; B01D 67/00045; B01D 67/0032; B01D 67/009; B01D 67/0093; F04B 19/006

See application file for complete search history.

(56) References Cited

U.S. PATENT DOCUMENTS

| | | |
|---|---|---|
| 7,727,399 B2 | 6/2010 | Leonard et al. |
| 8,147,562 B2 | 4/2012 | Vacanti et al. |
| 8,449,772 B2 | 5/2013 | Dirac et al. |
| 2002/0098124 A1 | 7/2002 | Bentsen et al. |
| 2009/0018629 A1 | 1/2009 | Yoshida et al. |
| 2010/0326914 A1 | 12/2010 | Drost et al. |
| 2014/0193799 A1 | 7/2014 | Borenstein et al. |
| 2014/0306371 A1 | 10/2014 | Guenther et al. |

OTHER PUBLICATIONS

Thompson, A.J., et al.; A Small-scale, Rolled-membrane Microfluidic Artificial Lung Desiged Towards Future Large Area Manufacturing; BioMicrofluidics 11, 024113 (2017); 12 pages.

Kniazeva, Tatiana et al., "A microfluidic respiratory assist device with high gas permeance for artificial lung applications", Biomedical Microdevices, Kluwer Academic Publishers, BO, vol. 13, No. 2, Nov. 27, 2010 (Nov. 27, 2010), pp. 315-323, XP01988529, ISSN: 1572-8781, DOI: 10.1007/S10544-010-9495-1.

Potkay, Joseph A., "The promise of microfluidic artificial lungs", Lab on a Chip, vol. 14, No. 21, Jan. 1, 2014 (Jan. 1, 2014), pp. 4122-4138, XP093122793, UK, issn: 1473-0197, DOI: 10.1039/C4LC00828F.

Willie, Wu, et al., "Omnidirectional Printing of 3D Microvascular Networks", Advanced Materials, VCH Publishers, DE, vol. 23, No. 24, Mar. 23, 2011 (Mar. 23, 2011), pp. H178-H183, XP071810833, ISSN: 0935-9648, DOI: 10.1002/ADMA.201004625.

FIG. 7A
FIG. 7B
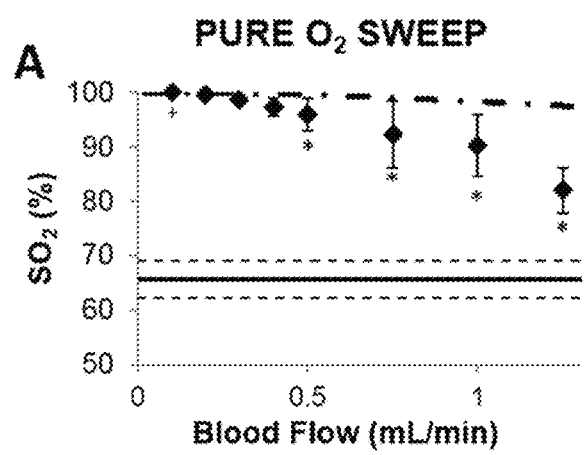
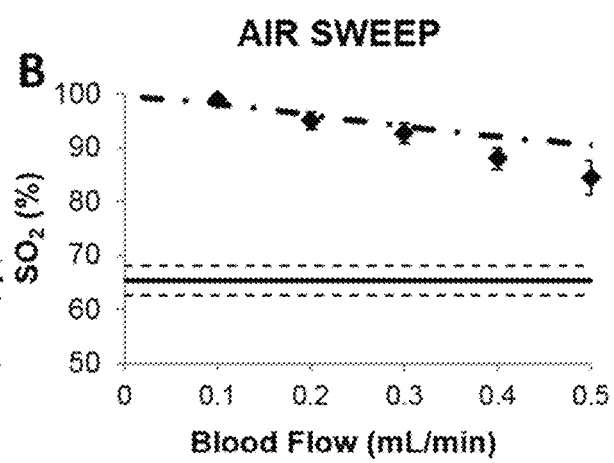
FIG. 7C
FIG. 7D

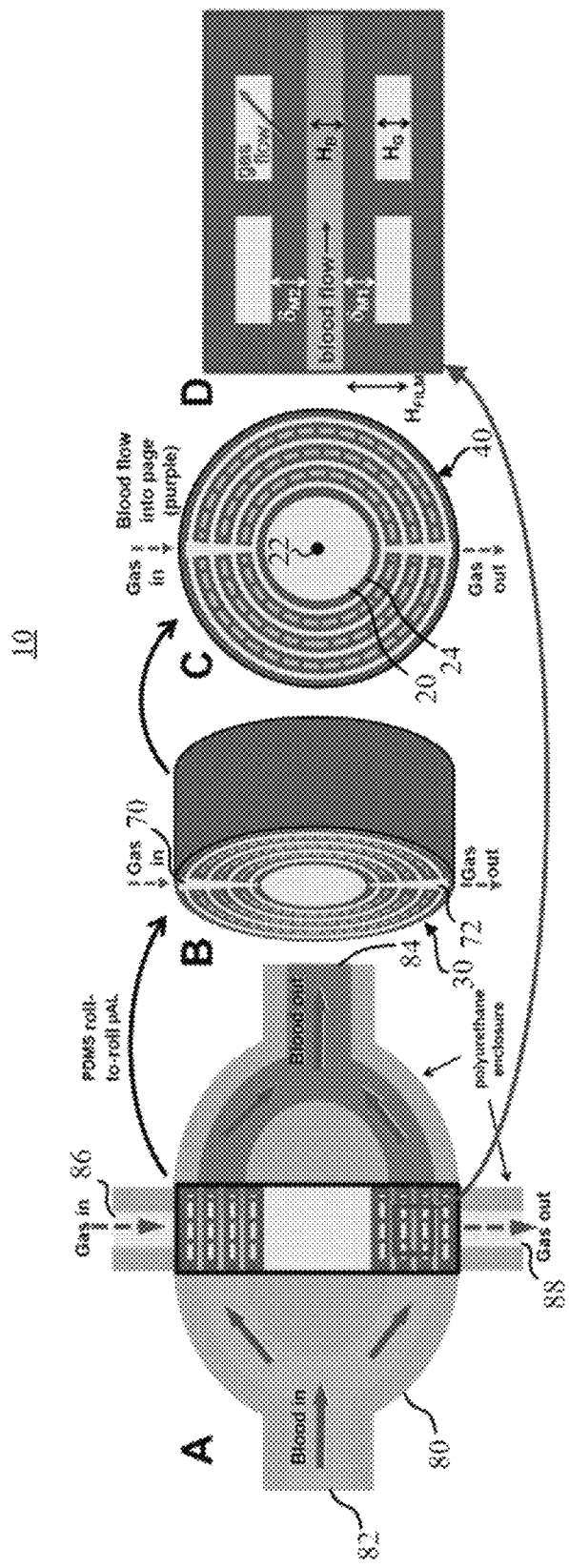

MICROFLUIDIC DIFFUSION DEVICES AND SYSTEMS, AND METHODS OF MANUFACTURING AND USING SAME

CROSS REFERENCE TO RELATED APPLICATIONS

This application is a divisional of U.S. patent application Ser. No. 16/499,999, filed Oct. 1, 2019, which claims priority to International Application No. PCT/US2018/025952, filed on Apr. 3, 2018, which claims the benefit of the filing date of U.S. Provisional Application No. 62/480,809, which was filed on Apr. 3, 2017. The entirety of each of these applications is hereby incorporated by reference herein.

STATEMENT REGARDING FEDERALLY SPONSORED RESEARCH

This invention was made with government support under Grant Nos. 1I01RX000390-01A1, 2I01RX000390-04A2, 1I21RX002403-01A1, and C3819C awarded by the U.S. Department of Veterans Affairs. The U.S. government has certain rights in the invention.

BACKGROUND

More than 33 million Americans are living with chronic lung disease; it is responsible for nearly 400,000 deaths every year and is a major disease associated with an increasing death rate. Acute respiratory distress syndrome (ARDS) has a 25-40% mortality rate and affects more than 190,000 Americans each year. Chronic obstructive pulmonary disease (COPD) affects 5% of American adults and approximately 16% of the veteran population. COPD is the fourth most prevalent disease in veterans and one of the most costly to the VA health care system. Over 500,000 service-connected respiratory disabilities have been diagnosed in veterans and 6.5% of Gulf War service-connected disabilities are respiratory system related. Operation Enduring Freedom and Operation Iraqi Freedom Veterans have been exposed to chemicals known to cause acute and chronic respiratory conditions including CARC paint and chromium dust. Other veterans have experienced acute lung injury and failure from blast injury or smoke inhalation. In total, over 2.3 million veterans reported "lung trouble" in the 2001 National Survey of Veterans.

In the clinical setting, positive pressure ventilation (i.e., mechanical ventilation) has been traditionally used to partially compensate for the pulmonary insufficiency caused by lung disease. However, the high airway pressures and oxygen concentrations can result in barotrauma, volutrauma, and biotrauma, and can exacerbate the original illness, even resulting in multi-organ failure. Artificial lung technologies have been developed to provide respiratory support without the drawback of ventilator-induced injury. In acute cases, artificial lungs provide respiratory support permitting the lung to heal while the patient rehabilitates. In chronic cases, artificial lungs serve as a bridge to transplant, increasing survival and improving quality of life. The Maquet Quadrox and Novalung iLA Membrane Ventilator represent the state-of-the-art in commercially-available artificial lung technologies. Both have a low resistance and can be driven by the natural heart. The Quadrox has recently been used in ambulatory ECMO in which the artificial lung, blood pump, computer, battery, and oxygen cylinder are mounted to a wheeled pole to provide limited mobility in the ICU setting. A single Quadrox has been used clinically for up to two months with systemic anticoagulation.

Despite advancements, treatment and outcomes with artificial lung systems remain unsatisfactory. Current systems permit minimal ambulation and their use is typically limited to the ICU. Truly portable systems that enable full ambulation are simply not possible with current technologies. Further, device-mediated complications including inflammation, device clotting, and hemolysis are common during treatment with current systems, especially in longer cases. Most devices have clinical lifetimes measured in days. Finally, current systems are limited to supporting the respiratory needs of a patient at rest. Thus, for artificial lungs to realize their potential for both long term respiratory support and more effective short term rehabilitation, significant improvements in biocompatibility, gas exchange, and portability must be made.

Microfluidic artificial lungs, artificial lungs that contain micron-scale flow channels and diffusion membranes, have been recently been investigated as a means to overcome the drawbacks of traditional artificial lung systems. Due to their reduced diffusion distances, microfluidic artificial lungs can achieve superior gas exchange efficiency, thereby enabling artificial lungs of reduced size, increasing portability and decreasing the blood contacting surface area (thereby increasing device lifetime and patient outcomes). Microfluidic artificial lungs can also contain blood flow paths that closely mimic those in the natural lung, thereby potentially increasing biocompatibility and lifetime. However, all microfluidic devices to date can only support a fraction of the blood flow needed for human applications and a means to easily and efficiently scale them up in size does not currently exist. Disclosed herein are exemplary microfluidic artificial lung topologies and manufacturing methods that can overcome this hurdle, thereby enabling the first human-scale microfluidic artificial lungs.

SUMMARY

Disclosed herein are microfluidic devices that are produced using a 3D-printing process. These microfluidic devices can include a liquid distribution pathway (e.g., a blood distribution pathway) extending along a liquid flow axis and include at least one liquid inlet (e.g., blood inlet), at least one liquid outlet (e.g., blood outlet), and a capillary bed positioned between the at least one liquid inlet and the at least one liquid outlet relative to the liquid flow axis. The capillary bed can include a plurality of capillary elements defining respective lumens that are in fluid communication with the at least one liquid inlet and the at least one liquid outlet. The microfluidic devices can also form a gas flow pathway extending along a gas flow axis that is perpendicular or substantially perpendicular to the liquid flow axis. The gas flow pathway can intersect at least a portion of the capillary bed to define a gas exchange region. The plurality of capillary elements can be formed from a material that permits diffusion of gas from the gas flow pathway into liquid (e.g., blood) within the plurality of capillary elements.

Also disclosed herein are microfluidic devices (e.g., artificial lung devices) that can be produced using a roll-to-roll process as further disclosed herein. The microfluidic devices can comprise a cylindrical substrate and have a central axis and an outer surface. The microfluidic devices can also include a patterned membrane rolled circumferentially over the outer surface of the cylindrical substrate to define a plurality of concentric membrane layers extending radially outwardly from the central axis of the cylindrical substrate.

At least one membrane layer of the plurality of concentric membrane layers can be patterned to define a plurality of gas flow channels that are configured to receive a sweep gas, and at least one membrane layer of the plurality of concentric membrane layers can be patterned to define a plurality of liquid (e.g., blood) flow channels that are configured to receive liquid (e.g., blood). The at least one membrane layer can permit diffusion of gas from the plurality of gas flow channels into the blood within the plurality of liquid (e.g., blood) flow channels.

Methods of using and manufacturing the disclosed microfluidic devices are also disclosed. Additional aspects of the invention will be set forth, in part, in the detailed description, and claims which follow, and in part will be derived from the detailed description, or can be learned by practice of the invention. It is to be understood that both the foregoing general description and the following detailed description are exemplary and explanatory only and are not restrictive of the invention as disclosed.

BRIEF DESCRIPTION OF THE DRAWINGS

FIG. 3A shows the horizontal device cross-section. FIG. 3B shows the vertical device cross-section. FIG. 3C shows a cross-section view of the branching blood network. FIG. 3D shows a top view of the capillary bed. Relevant design variables are shown in FIG. 3D.

FIG. 5A shows a top view illustration of the design of the rolled membrane showing the blood flow path (bottom). FIG. 5B shows a side view illustration and fabrication of the rolled membrane (top) and finished device cross-section (bottom).

FIG. 6A shows an image of the beginning of the rolling process in which the silicone tubing substrate has been bonded to the edge of the PDMS sheet. FIG. 6B shows a rolled device having a polymer sheet, consisting of both blood and gas flow channels (as illustrated with dyed water flowing through channels), wrapped around a cylindrical substrate in a manner similar to roll-to-roll polymer sheet processing, as disclosed herein. FIG. 6C shows in image of the cross-section of the rolled device. FIG. 6D shows the completed device before attachment of connectors.

FIGS. 7A-D show the gas transfer performance of rolled membrane devices (n=6) employing $O_2$ (FIGS. 7A, 7C) or air (FIGS. 7B, 7D) as the sweep gas and the $CO_2$ removal data for devices using either $O_2$ or air sweep gas (n=6). Measured $O_2$ saturation (FIGS. 7A, 7B) and $pCO_2$ (FIGS. 7C, 7D) of bovine blood are plotted along with theoretical values based on device design. Error bars represent standard error of measured values. Dashed line represents ±standard error of measured inlet blood gas concentrations. +n=5 *n=3.

FIGS. 11A-H show an exemplary human-scale microfluidic artificial lung formed by roll-to-roll (R2R) manufacturing and its performance metrics, as disclosed herein. FIG. 11A provides a cross-sectional view of the R2R PDMS microfluidic artificial lung (black outline) inside a custom polyurethane housing (light grey). FIGS. 11B-C are cross-sectional views of the PDMS microfluidic artificial lung showing gas and liquid flow channels. FIG. 11D is a cross-sectional view of the gas exchange interface showing relevant dimensions. FIGS. 11E-H are plots of blood contacting surface area (FIG. 11E), capillary wall shear stress (FIG. 11F), blood priming volume (FIG. 11G), and gas-side pressure drop (FIG. 11H) as a function of capillary height. Capillary pressure drop=50 mmHg; rated blood flow=1 L/min.

DETAILED DESCRIPTION

Figure 1:
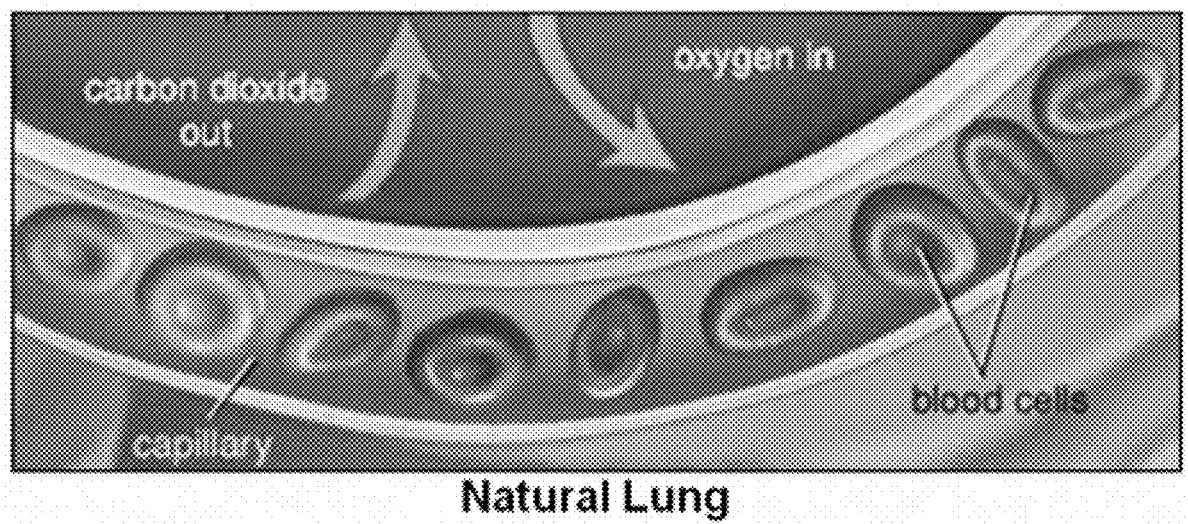
FIG. 1 shows the size of the basic unit of gas exchange in the natural lung. A red blood cell is shown in the figure for reference.

The present disclosure can be understood more readily by reference to the following detailed description of the invention, the figures and the examples included herein.

Before the present compositions and methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

Definitions

As used in the specification and the appended claims, the singular forms "a," "an" and "the" include plural referents unless the context clearly dictates otherwise.

The word "or" as used herein means any one member of a particular list and also includes any combination of members of that list.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

Ranges can be expressed herein as from "about" or "approximately" one particular value, and/or to "about" or "approximately" another particular value. When such a range is expressed, a further aspect includes from the one particular value and/or to the other particular value. Similarly, when values are expressed as approximations, by use of the antecedent "about," or "approximately," it will be understood that the particular value forms a further aspect. It will be further understood that the endpoints of each of the ranges are significant both in relation to the other endpoint and independently of the other endpoint. It is also understood that there are a number of values disclosed herein and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

As used herein, the terms "optional" or "optionally" mean that the subsequently described event or circumstance may or may not occur and that the description includes instances where said event or circumstance occurs and instances where it does not.

As used herein, the term "subject" refers a human. In some aspects, the subject as described herein can be an individual with a condition, disease or disorder that can be treated using a microfluidic diffusion device as disclosed herein. The term "subject" includes adults, children, adolescents and newborn subjects.

As used herein, the term "patient" refers to a subject afflicted with a disease or disorder that can be treated using a microfluidic diffusion device as disclosed herein. The term "patient" includes human subjects. In some aspects of the disclosed methods, the "patient" has been diagnosed with a need for an artificial lung device as disclosed herein.

As used herein, the term "substantially" can be indicative of a tolerance from a stated characteristic that would be acceptable to one of ordinary skill in the art. Optionally, the term "substantially" can be indicative of a tolerance of up to 15% above or below a stated characteristic, of up to 10% above or below a stated characteristic, or up to 5% above or below a stated characteristic. For example, if a first axis is "substantially parallel" to a second axis, then it is understood that the first axis can be within up to 15%, within up to 10%, or within up to 5% of being parallel to the second axis.

As used herein, the term "micro" generally refers to a size scale ranging between about 1 μm and about 1 mm. The term "microfluidic" generally means the confinement or operation of flows at this size domain (i.e., between about 1 μm and about 1 mm). As used herein, the "diffusion device" can refer to a diffusion device with precisely defined liquid and/or gas flow paths (typically formed using microfabrication methods such as those disclosed herein) in which the smallest dimensions of the flow paths and diffusion membrane are less than approximately 250 μm and optionally between about 10 μm and 100 μm.

Introduction

Figure 2A:
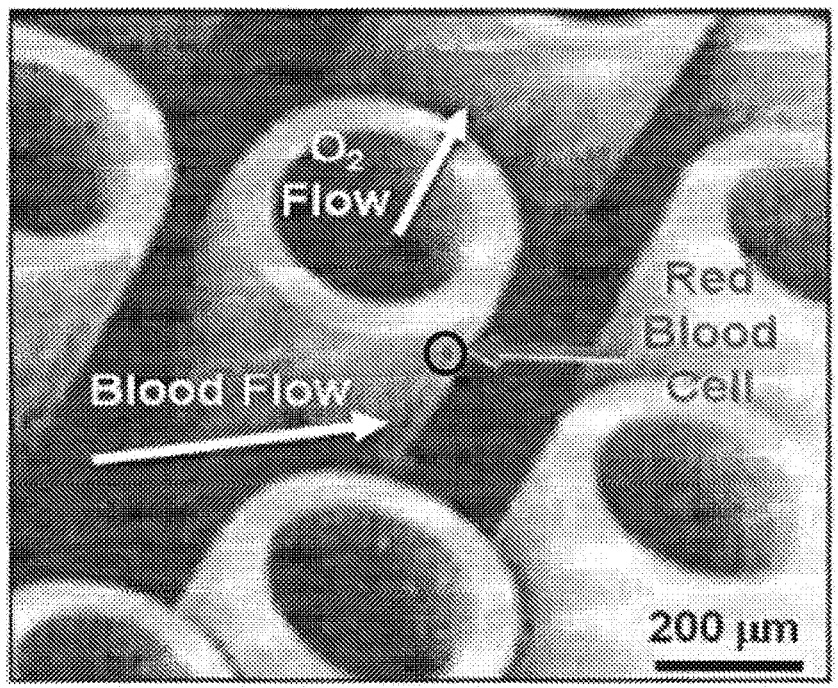
FIGS. 2A-B show the size of the basic unit of gas exchange in conventional artificial lungs and in microfluidic artificial lungs. A red blood cell is shown in FIG. 2A (located within the encircled region labeled as "red blood cell") and in FIG. 2B (labeled as "red blood cell").
Figure 2B:
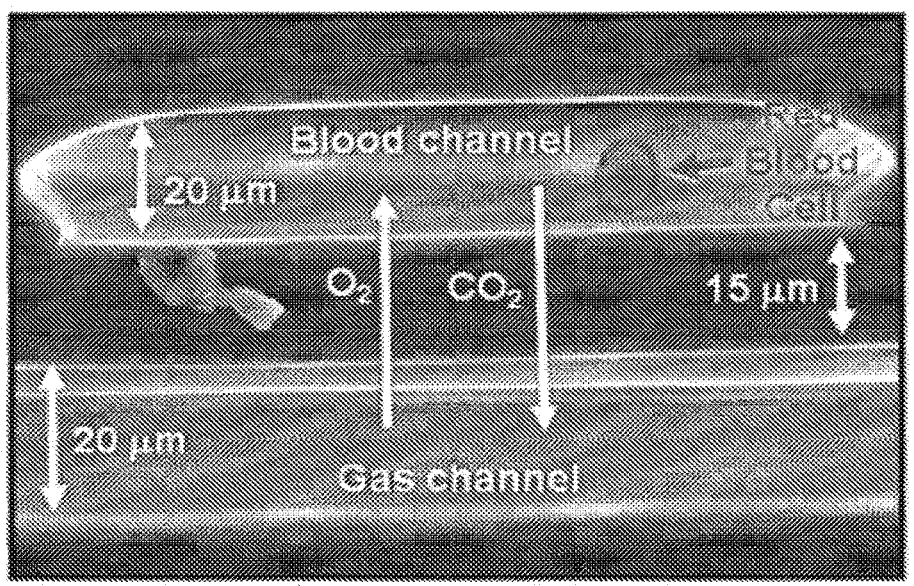

Artificial lungs mimic the function of natural lungs by adding $O_2$ to and removing $CO_2$ from the blood (FIGS. 1 and 2A-2B). First, blood is routed from the body to the artificial lung. Inside the artificial lung, blood travels along one side of a gas permeable membrane. Pure oxygen typically flows along the other side of the membrane and is transferred to the blood by diffusion through the membrane. Carbon dioxide diffuses out of the blood due to a lower partial pressure in the gas stream. The oxygenated blood is then returned to the body. Current commercial devices contain either a silicone sheet membrane or, more predominantly, hollow fiber membranes (FIG. 2A). Blood flows on the outside of the fibers in a circuitous path that creates mixing and enhances gas transfer. The sweep gas (typically pure $O_2$) flows inside the hollow fibers and diffuses through the porous membrane and into the blood, enriching the blood with $O_2$. In addition, $CO_2$ diffuses out of the blood due to a lower partial pressure in the gas stream.

The performance and biocompatibility of current artificial lungs is limited. New microfluidic devices have demonstrated potential improvement in both of these areas, but current manufacturing techniques are not suitable for large area, human scale devices. Further, the planar nature of current microfabrication techniques limits potential design topologies leading to inefficient blood flow networks.

Microfluidic Diffusion Devices: In contrast to current artificial lung devices, the microfluidic diffusion devices disclosed herein can provide improved gas exchange, portability, and biocompatibility by: 1) drastically decreasing diffusion distance and increasing surface-area-to-volume ratio in small diameter artificial capillaries (FIG. 2B), and 2) providing blood flow networks that mimic the natural cellular environment.

Despite the promising potential of current small-scale microfluidic devices, a manufacturing technique to efficiently scale them up in size for human application does not currently exist. Further, because current microfabrication techniques can only effectively create two dimensional structures, blood flow paths and gas exchange cannot be fully optimized. As an example of relevance, a microfluidic artificial lung with 10 μm artificial capillaries that exhibited record gas exchange efficiency was reviewed, but the gas exchange region accounted for 6% of the total blood contacting surface area and 2% of the blood volume of the device (due to the inefficient 2D blood flow path). Thus, a method to rapidly and simply create large area diffusion devices (e.g., microfluidic lungs) with three-dimensional (3D) topologies would thus represent a breakthrough in the field and would overcome a major barrier to the clinical application of microfluidic diffusion devices (e.g., artificial lungs).

In exemplary aspects, the disclosed microfluidic diffusion devices can be provided as human-scale microfluidic artificial lungs, which can: 1) include surface areas and blood priming volumes that are a fraction of current technologies, thereby decreasing device size and reducing the body's immune response; 2) contain blood flow networks in which cells and platelets experience pressures, shear stresses, and branching angles that copy those in the human lung, thereby improving biocompatibility; 3) operate efficiently with room air, eliminating the need for gas cylinders and complications associated with hyperoxemia; 4) exhibit biomimetic hydraulic resistances, enabling operation with natural pressures and eliminating the need for blood pumps (depending on application); and 5) provide increased gas exchange capacity enabling respiratory support for active patients.

As described herein, artificial lung technology has the potential to improve rehabilitation of patients suffering from respiratory disabilities through: 1) improved gas transfer performance compared to current devices to permit respiratory support of active patients; 2) increased biocompatibility to increase device lifetime, permit long-term treatment, and increase patient health; and, 3) increased portability to permit ambulatory care and improved patient quality of life. After integration into various complete systems, it is contemplated that the disclosed devices can provide lung rest for patients suffering from acute pulmonary disabilities, serve as a bridge to transplant for patients with chronic lung disease and lung cancer, and lead to the development of the first implantable artificial lung for semi-permanent support. In addition, the device can be used in portable heart-lung machines for forward surgical care on the battlefield and elsewhere.

Microfluidic Diffusion Devices

Disclosed herein are microfluidic diffusion devices having a gas flow pathway and a liquid flow pathway. As further described herein, the disclosed microfluidic diffusion devices can be formed by three-dimensional (3D) printing or by a roll-to-roll process. The gas flow pathway and the liquid flow pathway of the disclosed diffusion devices can be separated by a membrane that permits diffusion of gas from the gas flow pathway into the liquid flow pathway and/or that permits diffusion of liquid from the liquid flow pathway into the gas flow pathway. Optionally, in exemplary aspects, at least one of the gas flow pathway and the liquid flow pathway can have a smallest dimension of less than 250 µm.

Unlike current devices and manufacturing techniques, it is contemplated that the disclosed diffusion devices and their associated manufacturing techniques (roll-to-roll and 3D-printing) can be used to efficiently build large-scale microfluidic diffusion devices (e.g., artificial lungs) that are suitable for human applications or other large-scale microfluidic diffusion applications. Optionally, when the microfluidic diffusion devices are designed for clinical applications (e.g., artificial lung applications), the liquid flow pathway can be configured to receive blood, the gas flow pathway can be configured to receive a gas comprising oxygen (air or oxygen gas), and the membrane can be configured to permit diffusion of oxygen into the liquid flow pathway.

While the diffusion devices are described herein as a microfluidic device and specifically described as an artificial lung device, it is to be understood that the disclosed diffusion devices, systems, and methods are not limited to use as microfluidic devices or, more particularly, as artificial lung devices. It is contemplated that the disclosed diffusion devices can be suitable for use in many other devices such as, without limitation, gas purification systems, dialysis or artificial kidney systems, carbon capture systems, and the like. The disclosed structure is a large-area diffusion device with many applications, particularly those in which it is necessary to provide diffusion through a membrane from one species (gas or liquid) to another species (gas or liquid).

3D-Printed Microfluidic Devices

Figures 3A, 3B, 3C, 3D:
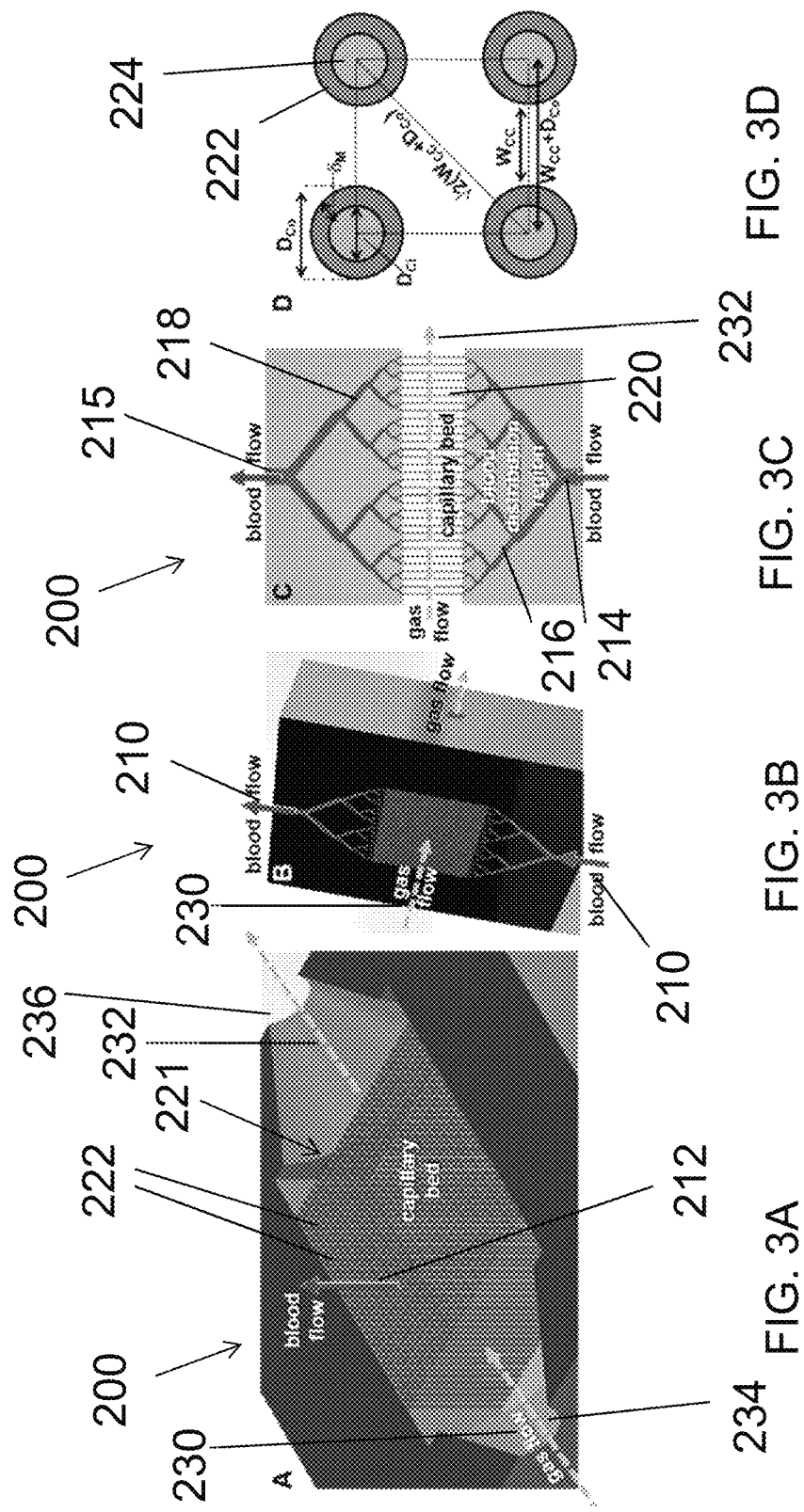
FIGS. 3A-D show the design of one exemplary embodiment of a 3D-printed microfluidic lung.

Disclosed herein, and with reference to FIGS. 3A-3D, are three-dimensionally printed microfluidic diffusion devices. In exemplary aspects, a three-dimensionally printed microfluidic diffusion device 200 as disclosed herein can comprise a liquid (e.g., blood) distribution pathway 210 and a gas flow pathway 230. The liquid (e.g., blood) distribution pathway 210 can extend along a liquid flow axis 212 and comprise at least one liquid inlet 214 (optionally, a single inlet), at least one liquid outlet 215 (optionally, a single outlet), and a capillary bed 220. As used herein, the term "capillary bed" generally refers to a plurality of small capillary-like elements (i.e., vessels) that receive liquid as disclosed herein; although not required, the "capillary bed" can receive and permit flow of blood. The capillary bed 220 can be positioned between the at least one liquid inlet 214 and the at least one liquid outlet 215 relative to the liquid flow axis 212. In exemplary aspects, the capillary bed 220 can comprise a plurality of capillary elements 222 defining respective lumens 224 that are in fluid communication with the at least one liquid inlet 214 and the at least one liquid outlet 215. The gas flow pathway 230 can extend along a gas flow axis 232 that is perpendicular or substantially perpendicular to the liquid flow axis 212. As shown in FIG. 3A, the gas flow pathway 230 can have a gas inlet 234 and a gas outlet 236. As shown in FIGS. 3A-3C, the gas flow pathway 230 can intersect at least a portion of the capillary bed 220 to define a gas exchange region 221. In order to permit gas exchange, it is contemplated that the plurality of capillary elements 222 can be formed (i.e., printed) from a material that permits diffusion of gas from the gas flow pathway 230 into liquid (e.g., blood) within the plurality of capillary elements 222.

Optionally, the plurality of capillary elements 222 can be oriented parallel or substantially parallel to the liquid flow axis 212. However, it is contemplated that other orientations of the capillary elements can be used. For example, it is contemplated that some capillary elements can be oriented in different directions than other capillary elements.

Optionally, the plurality of capillary elements 222 can be evenly or substantially evenly distributed within the capillary bed 220. However, it is contemplated that non-homogenous (heterogeneous) or random distributions of capillary elements 222 can be used as desired. In diffusion devices in which a homogenous distribution of capillary elements is desired, it is contemplated that the plurality of capillary elements can be arranged in a plurality of rows and columns in which the spacing between sequential capillary elements in each column and the spacing between sequential capillary elements in each row is uniform or substantially uniform. As used herein, in exemplary aspects, the term "spacing" can refer to a distance, within a reference plane that is perpendicular to the liquid flow axis, between center points of respective capillary elements.

In exemplary aspects, within the gas exchange region 221, portions of the gas flow pathway 230 circumferentially surround at least a portion of an outer surface of each capillary element 222 of the plurality of capillary elements.

Optionally, in these aspects, portions of the gas flow pathway 230 can circumferentially surround the entire length of each capillary element 222. Optionally, as shown in in FIG. 3A, it is contemplated that the gas flow pathway 230 can have a variable width or diameter moving along the gas flow axis 232. For example, it is contemplated that the width or diameter of the gas flow pathway 230 can increase as it approaches the capillary bed 220 from the gas inlet 234 and the gas outlet 236.

In further exemplary aspects, the liquid (e.g., blood) distribution pathway 210 can further comprise first and second liquid (e.g., blood) distribution regions 216, 218 that are respectively positioned between the at least one liquid inlet 214 and the capillary bed 220 and between the capillary bed and the at least one liquid outlet 215. Optionally, in these aspects, it is contemplated that the liquid distribution regions 216, 218 can be printed to mimic the patterns of physiological blood distribution networks, including the number, shape, and orientation of branches and sub-branches extending outwardly from the capillaries. In exemplary aspects, as shown in FIG. 3C, it is contemplated that the first and second liquid distribution regions 216, 218 can comprise a plurality of branches and sub-branches that progressively decrease in inner diameter until reaching the plurality of capillary elements 222 of the capillary bed 220.

Optionally, in exemplary aspects, the lumen 224 of each capillary element 222 can have an inner diameter ranging from about 5 μm to about 250 μm, from about 10 μm to about 200 μm, or more particularly from about 30 μm to about 100 μm. However, it is contemplated that the inner diameter of each capillary element can be selectively varied depending upon the particular application and other variables, such as the length of the capillary element. In further exemplary aspects, it is contemplated that the length of each capillary element relative to the liquid flow axis can depend largely on pressure drop and the target application, and can range from at least 300 μm to up to 3 mm or longer.

In further exemplary aspects, it is contemplated that at least the plurality of capillary elements 222 can comprise photosensitive polydimethylsiloxane (PDMS). Optionally, in these aspects, the entire liquid distribution pathway 210 can be formed from PDMS. While PDMS is disclosed as a suitable material for the disclosed 3D-printed devices, it is contemplated that any gas-permeable or micro/nano porous material that is capable of being 3D-printed can be used.

As further disclosed herein, it is contemplated that a three-dimensional printer can be used to form the previously described microfluidic diffusion devices 200. It is contemplated that existing photosensitive materials, such as a previously-developed photosensitive PDMS, can be used to produce the disclosed microfluidic diffusion devices 200 using a high-resolution 3D printer as is known in the art. A suitable example of such a high-resolution 3D printer is the high-resolution MC-2 polymer 3D printing system. It is contemplated that the ratio of photosensitive material (e.g., PDMS) to photoinitiator and the exposure dose can be modified to achieve suitable resolution and printing speed. The 3D printer system and photosensitive material can then be used to print the flow pathways as disclosed herein.

Rolled Diffusion Devices

Also disclosed herein, and with reference to FIGS. 5A-13, is a diffusion device 10 (optionally, a microfluidic diffusion device) that can be produced using a rolling or roll-to-roll process as disclosed herein. Such devices are generally referred to "rolled" devices or membranes herein. In exemplary aspects, the diffusion device 10 can be an artificial lung device, or more specifically, a rolled-membrane microfluidic artificial lung device. In some aspects, the artificial lung devices disclosed herein can be designed towards large area manufacturing. More specifically, the instant disclosure provides a new manufacturing technique to create new, rolled, cylindrical topology diffusion devices and the Examples provided herein demonstrate its application to a microfluidic artificial lung. The manufacturing technique can provide the ability to create large area microfluidic devices which can be automated to improve manufacturability. The methods disclosed herein can provide an automated method to simply create large area microfluidic diffusion devices for many applications.

Figure 5A:
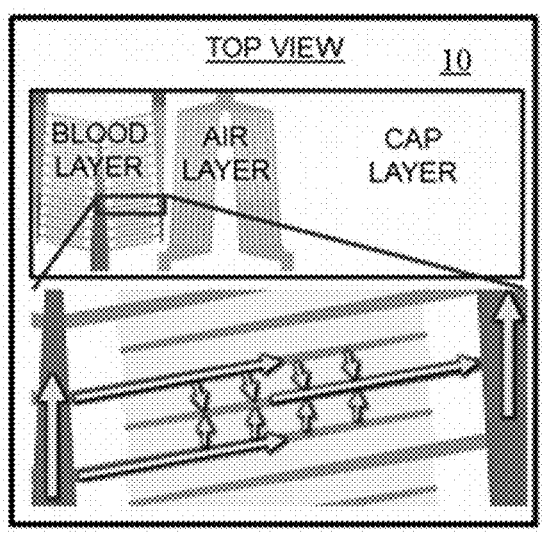
FIGS. 5A-B show different views of an exemplary rolled membrane device as disclosed herein.
Figure 5B:
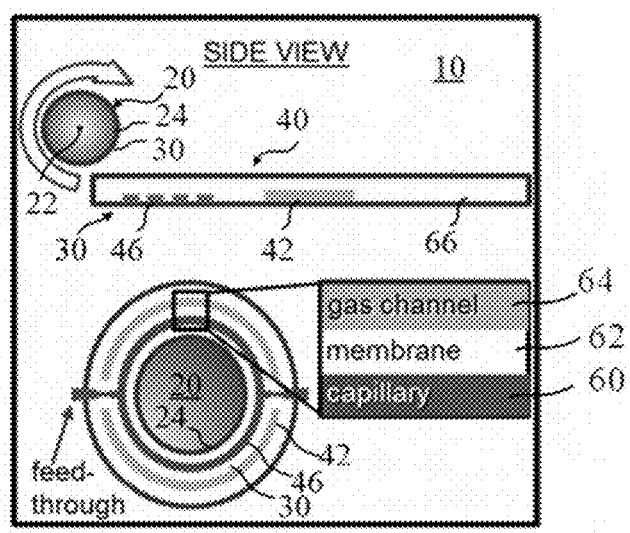

In one aspect, the microfluidic diffusion device 10 can comprise a cylindrical substrate 20 having a central axis 22 and an outer surface 24. In exemplary aspects, the cylindrical substrate 20 can comprise a tubular structure, such as silicone tubing. However, it is contemplated that other cylindrical structures can be used, provided they are configured for bonding or other secure attachment to membrane layers as further disclosed herein. In another aspect, the microfluidic diffusion device 10 can comprise a patterned membrane 30 rolled circumferentially over the outer surface 24 of the cylindrical substrate 20 to define a plurality of concentric membrane layers 40 extending radially outwardly from the central axis 22 of the cylindrical substrate 20. As used herein, the term "rolled circumferentially" is intended to encompass structures resulting from (a) the rolling of the patterned membrane around a cylindrical substrate while the cylindrical substrate is in a fixed position (but free to rotate), such as in a roll-to-roll process as disclosed herein, as well as (b) the rolling of a cylindrical substrate along the length of a patterned membrane as disclosed herein. In a further aspect, at least one membrane layer of the plurality of concentric membrane layers 40 can be patterned to define a plurality of gas flow channels 42 that are configured to receive a gas (e.g., a sweep gas such as oxygen gas). In another aspect, at least one membrane layer of the plurality of concentric membrane layers 40 can be patterned to define a plurality of liquid flow channels 46 (e.g., blood flow channels) that are configured to receive liquid (e.g., blood). While the present disclosure refers to such channels as "liquid flow channels," it is to be understood that in exemplary aspects, the liquid flow channels described herein can be blood flow channels, and thus, any description provided herein that relates to such liquid flow channels can also apply more specifically to blood flow channels. In these aspects, the at least one membrane layer 40 can permit diffusion of gas from the plurality of gas flow channels 42 into the liquid (e.g., blood) within the plurality of liquid flow channels 46. Additionally, or alternatively, the at least one membrane layer 40 can permit diffusion of liquid from the plurality of liquid channels 46 into the gas within the plurality of gas flow channels 42. Additionally, or alternatively, the at least one membrane layer 40 can permit diffusion of liquid among different liquid channels of the plurality of liquid channels. It is contemplated that, in some aspects, and as shown in FIGS. 5A-5B for example, at least one membrane layer of the plurality of concentric membrane layers 40 does not comprise gas or liquid flow channels 42, 46. In further aspects, as shown in FIGS. 5A-5B, the plurality of gas flow channels 42 and the plurality of liquid flow channels 46 can be engraved in respective portions of the patterned membrane 30. Although some particular configurations of concentric membrane layers are disclosed herein, it is contemplated that any desired number of concentric membrane layers can be used. In exemplary aspects, it is contemplated that as many as 100, 200, 300, 400, or 500 concentric membrane layers can be used to produce a microfluidic diffusion device.

It is contemplated that the patterned member can comprise a single contiguous sheet of material. Optionally, the patterned membrane 30 can comprise a web or film of polydimethylsiloxane (PDMS). In exemplary aspects, the patterned membrane 30 can have a maximum (radial) thickness ranging from about 10 µm to about 250 µm, or more particularly from about 50 µm to about 150 µm. In further aspects, the plurality of gas flow channels 42 can be patterned to have a thickness ranging from about 10 µm to about 250 µm, or more particularly from about 30 µm to about 120 µm. The plurality of liquid flow channels 46 can be patterned to have a thickness ranging from about 5 µm to about 250 µm, or more particularly from about 5 µm to about 95 µm. Thus, in some optional aspects, one or more gas flow channels can extend completely through the thickness of the patterned membrane. Additionally, or alternatively, in other optional aspects, one or more liquid flow channels can extend completely through the thickness of the patterned membrane. However, in many applications, it is understood that the liquid flow channels 46 and the gas flow channels 42 only extend partially into the thickness of the membrane.

In further aspects, the plurality of concentric membrane layers 40 can comprise a liquid flow layer 60 (e.g., a blood flow layer) bonded to the outer surface 24 of the cylindrical substrate 20 and comprising the plurality of liquid flow channels 46. It is to be understood that the liquid flow layer described herein can be a blood flow layer, and thus, any description provided herein that relates to the liquid flow layer can also apply more specifically to a blood flow layer.

The plurality of concentric membrane layers 40 can also comprise a gas flow layer 64 (e.g., an air layer) positioned radially adjacent to the liquid flow layer 60 and bonded to the liquid flow layer. The gas flow layer 64 can comprise the plurality of gas flow channels 42 as further disclosed herein. Optionally, the plurality of concentric membrane layers 40 can further comprise a capping layer 66 positioned radially outwardly of the gas flow layer 64 and bonded to the gas flow layer to cap the plurality of gas flow channels 42. In these aspects, the capping layer 66 does not comprise gas or liquid flow channels. Additionally, the capping layer 66 can enclose the plurality of gas flow channels 42. In these aspects, the plurality of gas flow channels 42 and the plurality of liquid flow channels 46 can be oriented parallel or substantially parallel to the central axis 22. Although disclosed herein as capping a gas flow layer 64, it is contemplated that a capping layer 66 can be positioned radially outward of a liquid flow layer 60 to likewise cap or enclose the liquid flow channels of a liquid flow layer. It should also be understood that the capping layer 66 as disclosed herein can be positioned as an outermost layer of a diffusion device having any desired number of membrane layers. It should further be understood that a capping layer 66 can be provided as an intermediate layer positioned radially between sequentially rolled membrane layers.

In exemplary aspects, and as further disclosed herein, it is contemplated that the plurality of liquid flow channels 46 and the plurality of gas flow channels 42 need not extend through the thickness of the membrane. In these aspects, and as shown in FIG. 5B, it is contemplated that as the patterned membrane is rolled onto a substrate as disclosed herein, portions of the membrane underlying the patterned flow channels (before rolling) can create circumferential (intermediate) barriers (diffusion regions) between the flow channels of adjacent membrane layers. It is further contemplated that, when the patterned surface of the membrane is farther away from the substrate (i.e., the un-patterned surface of the membrane is spaced radially inwardly from the patterned surface of the membrane) (see FIG. 5B), then the portions of the membrane defining the intermediate barriers can contact and cover or "cap" the flow channels defined on the patterned surface of an underlying membrane layer (that is positioned radially inwardly from the membrane layer defining the intermediate barrier). For example, as shown in FIG. 5B, portions of the membrane of gas flow layer 64 that underlie the formed gas flow channels 42 can form an intermediate barrier 62 that covers or "caps" the liquid flow channels 46 of the underlying liquid flow layer 60. In other aspects, it is further contemplated that, when the patterned surface of the membrane is closer to the substrate than the opposing un-patterned surface (see FIG. 12), the portions of the flow layers the portions of the membrane defining the intermediate barriers can enclose the bottom (inwardly facing) portions of flow channels defined on the patterned surface of an overlying membrane layer (that is positioned radially outwardly from the membrane layer defining the intermediate barrier). In these aspects, it is still further contemplated that the substrate 20 can enclose the flow channels of the most inwardly positioned membrane layer. In use, the intermediate barriers can permit diffusion of gas from the plurality of gas flow channels 42 into the plurality of liquid flow channels 46. However, it is contemplated that the intermediate barriers 62 can provide any desired liquid/gas diffusion characteristics. Additionally, it is contemplated that in configurations in which the gas or liquid flow channels of an outermost layer of the diffusion device do not fully penetrate through the membrane, then a portion of the membrane positioned radially outward of the channels can define the outer surface of the diffusion device such that a capping layer is unnecessary.

Optionally, in some aspects, the plurality of concentric membrane layers 40 can comprise a plurality of gas flow layers 64, with each gas flow layer 64 comprising a portion of the plurality of gas flow channels 42. Additionally, the plurality of concentric membrane layers 40 can comprises a plurality of liquid flow layers 60, with each liquid flow layer 60 comprising a portion of the plurality of liquid flow channels 46. Optionally, in these aspects, the gas flow layers 64 and the liquid flow layers 60 can be positioned in an alternating pattern moving radially outwardly from the central axis 22. However, it is contemplated that any desired sequence of membrane layers can be used. For example, it is contemplated that the plurality of concentric membrane layers can comprise a plurality of sequentially radially positioned liquid flow layers or a plurality of sequentially radially positioned gas flow layers. Optionally, it is contemplated that the flow channels of each respective flow layer can be separated from the flow channels of sequentially radially positioned flow layers by an intermediate barrier (diffusion region) defined by a membrane layer of the plurality of membrane layers. Optionally, in still further aspects, it is contemplated that the plurality of concentric membrane layers can further comprise at least one intermediate layer that is devoid of flow channels and that is positioned radially between other membrane layers of the plurality of concentric membrane layers.

In further aspects, the plurality of gas flow channels 42 can extend circumferentially about the central axis 22, and the plurality of liquid flow channels 46 can be oriented parallel or substantially parallel to the central axis 22. It is contemplated that the diffusion device 10 can further comprise a gas inlet channel 70 and a gas outlet channel 72. The gas inlet channel 70 can extend radially from an outer surface 24 of the patterned membrane 30 toward the cylindrical substrate 20. The gas outlet channel 72 can extend radially from an outer surface 24 of the patterned membrane 30 toward the cylindrical substrate 20. Both the gas inlet channel 70 and the gas outlet channel 72 can be positioned in fluid communication with at least a portion of the plurality of gas flow channels 42.

Alternatively, in other aspects, the plurality of gas flow channels 42 can be oriented parallel or substantially parallel to the central axis 22, and the plurality of liquid flow channels 46 can extend circumferentially about the central axis 22.

In some aspects, the diffusion device 10 can further comprise a housing 80 that defines a liquid (e.g., blood) inlet 82, a liquid (e.g., blood) outlet 84, a gas inlet 86, and a gas outlet 88. In these aspects, the liquid (e.g., blood) inlet 82 and the liquid (e.g., blood) outlet 84 can be positioned in fluid communication with at least a portion of the plurality of liquid flow channels 46, and the gas inlet 86 and the gas outlet 88 can be positioned in fluid communication with at least a portion of the plurality of gas flow channels 42. Optionally, in some aspects, the liquid (e.g., blood) inlet 82 and the liquid (e.g., blood) outlet 84 can be oriented in substantial alignment with the central axis 22, and the gas inlet 86 and the gas outlet 88 can be oriented perpendicularly or substantially perpendicularly to the central axis 22.

Figure 13:
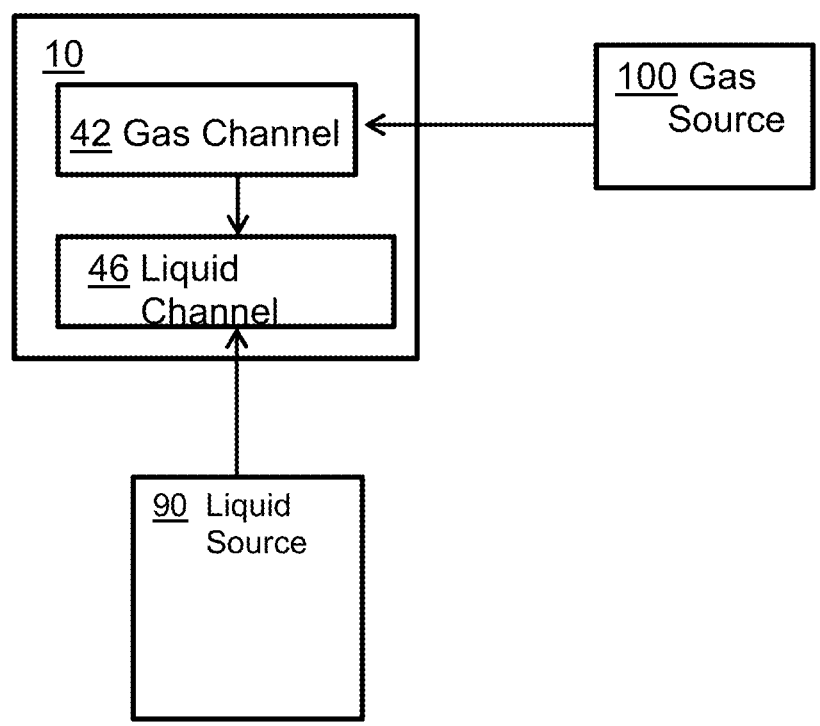
FIG. 13 is a schematic diagram of an exemplary diffusion device having liquid channels positioned in fluid communication with a liquid source and gas channels positioned in fluid communication with a gas source, as disclosed herein. In this example, diffusion of gas from the gas channels to the liquid channels is depicted using a flow arrow extending from the gas channel to the liquid channel.

Also disclosed herein, and as schematically illustrated in FIG. 13, are methods of using the disclosed diffusion device 10. In exemplary aspects, these methods can comprise positioning a source of liquid (e.g., a source of blood) 90 (e.g., such as a patient) in fluid communication with the plurality of liquid flow channels 46 of the diffusion device 10 disclosed herein. The methods can further include positioning the plurality of gas flow channels 42 of the diffusion device 10 in fluid communication with a source of gas 100. Following positioning of the gas flow channels 42, the gas from the source of gas 100 can diffuse from the plurality of gas flow channels 42 into liquid (e.g., blood) within the plurality of liquid flow channels 46. Optionally, in some aspects the source of gas 100 can be air surrounding the diffusion device 10. Alternatively, in other aspects, the source of gas 100 can be a container filled with oxygen (or other) gas. In further aspects, the disclosed methods can also comprise using conventional methods to selectively adjust at least one of a liquid flow rate (e.g., a blood flow rate), a gas flow rate, or a composition of the gas provided by the gas source.

Further disclosed herein are methods of forming a rolled microfluidic device as described herein. These methods can include patterning a membrane 120 to define a plurality of flow channels, and circumferentially rolling the patterned membrane 30 over an outer surface 24 of a cylindrical substrate 20 to define a plurality of concentric membrane layers 40 extending radially outwardly from a central axis 22 of the cylindrical substrate 20, thereby forming the device. Each flow channel of the plurality of flow channels can be configured to receive and permit flow of a fluid. As further described herein, at least one membrane layer of the plurality of concentric membrane layers 40 can be patterned to define a plurality of gas flow channels 42 that are configured to receive a gas (e.g., sweep gas), and at least one membrane layer of the plurality of concentric membrane layers 40 can be patterned to define a plurality of liquid (e.g., blood) flow channels 46 that are configured to receive liquid (e.g., blood). In some aspects, at least one membrane layer can permit diffusion of gas from the plurality of gas flow channels 42 into the blood within the plurality of liquid flow channels 46. Additionally, or alternatively, the at least one membrane layer 40 can permit diffusion of liquid from the plurality of liquid channels 46 into the gas within the plurality of gas flow channels 42. In these aspects, the cylindrical substrate 20 and the plurality of concentric membrane layers 40 cooperate to form a diffusion device 10, such as an artificial lung device.

As described herein, in some aspects, the patterned membrane 30 comprises a single contiguous sheet of material. Optionally, the patterned membrane 30 comprises a web or film of polydimethylsiloxane (PDMS). In these aspects, the method of forming the device can further include unrolling the membrane 120 before patterning of the membrane. In further aspects, the membrane can be patterned using a laser 130, and the plurality of flow channels can extend inwardly from an exposed surface of the membrane that is patterned by the laser 130. However, before patterning of the membrane 120, the membrane can be provided on a source roller 140 with a carrier layer 150. The source roller 140 can be rotated to advance the membrane and the carrier layer 150 in a processing direction, and an exposed surface 122 of the membrane can be patterned as the membrane and the carrier layer 150 are advanced in the processing direction. A first take-up roller 160 can then receive the patterned membrane 30, and a second take-up roller 170 can receive the carrier layer 150 after patterning of the membrane. In these aspects, the first take-up roller 160 can support the cylindrical substrate 20, which can be positioned over the take-up roller to receive sequential membrane layers during the rolling process as disclosed herein. After patterning of the membrane, the method can further include applying a surface treatment 180 to the exposed surface 122 of the membrane to activate bonding activity of the membrane. It is contemplated that the surface treatment 180 can include application of plasma, ultraviolet, ozone, corona, or chemical treatment.

It is contemplated that the patterned membrane 30 can have a maximum thickness ranging from about 10 µm to about 250 µm, or more particularly from about 50 µm to about 150 µm. In further aspects, the plurality of gas flow channels 42 can be patterned to have a thickness ranging from about 10 µm to about 250 µm, or more particularly from about 30 µm to about 120 µm. The plurality of liquid flow channels 46 can be patterned to have a thickness ranging from about 5 µm to about 250 µm, or more particularly from about 5 µm to about 95 µm. Optionally, in some aspects, the plurality of gas flow channels 42 and the plurality of liquid flow channels 46 can be engraved in respective portions of the patterned membrane 30.

In some aspects, at least one membrane layer of the plurality of concentric membrane layers 40 does not comprise gas or liquid flow channels 42, 46. In further aspects, as described herein, the plurality of concentric membrane layers 40 can be rolled to form a liquid flow layer, a gas flow layer, and a capping layer. Optionally, the capping layer can define the outer surface of the device. Alternatively, additional membrane layers can be positioned radially outwardly of the capping layer.

In other aspects, the plurality of concentric membrane layers 40 can comprise: a plurality of gas flow layers 64, each gas flow layer comprising a portion of the plurality of gas flow channels 42; and a plurality of liquid flow layers 60, each liquid flow layer comprising a portion of the plurality of liquid flow channels 46. In these aspects, the gas flow layers 64 and the liquid flow layers 60 can be positioned in an alternating pattern moving radially outwardly from the central axis 22. In further aspects, the plurality of gas flow channels 42 can extend circumferentially about the central axis 22, and the plurality of liquid flow channels 46 can be oriented parallel or substantially parallel to the central axis 22. In these aspects, the method of forming the device can also include forming a gas inlet channel 70 extending radially from an outer surface 24 of the patterned membrane 30 toward the cylindrical substrate 20, such that the gas inlet channel 70 is positioned in fluid communication with at least a portion of the plurality of gas flow channels 42. The method can further include forming a gas outlet channel 72 extending radially from an outer surface 24 of the patterned membrane 30 toward the cylindrical substrate 20, such that the gas outlet channel 72 is positioned in fluid communication with at least a portion of the plurality of gas flow channels 42. In exemplary aspects, it is contemplated that the gas inlet channel and the gas outlet channel can be formed by selectively patterning the membrane layers to cooperatively form the gas inlet channel and the gas outlet channel upon circumferential rolling of the patterned membrane layers. Additionally, or alternatively, it is contemplated that the gas inlet and the gas outlet can be formed by patterning or cutting (e.g., physical, laser, or otherwise) through the membrane layers after rolling the device.

Optionally, in some aspects, the method of forming the device can further comprise positioning the device within a housing 80, the housing defining a liquid (e.g., blood) inlet 82, a liquid (e.g., blood) outlet 84, a gas inlet 86, and a gas outlet 88. In these aspects, the liquid inlet 82 and the liquid outlet 84 can be positioned in fluid communication with at least a portion of the plurality of liquid flow channels 46, and the gas inlet 86 and the gas outlet 88 can be positioned in fluid communication with at least a portion of the plurality of gas flow channels 42. In further aspects, the liquid inlet 82 and the liquid outlet 84 can be oriented in substantial alignment with the central axis 22, and the gas inlet 86 and the gas outlet 88 can be oriented perpendicularly or substantially perpendicularly to the central axis 22. Alternatively, the liquid inlet 82 and the liquid outlet 84 can be oriented perpendicularly or substantially perpendicularly to the central axis 22, and the gas inlet 86 and the gas outlet 88 can be oriented in substantial alignment with the central axis.

Additional non-limiting details and exemplary uses and applications of the disclosed diffusion devices are disclosed in following Examples.

EXAMPLES

Artificial lungs have been successfully used in the clinic for multiple decades to supplement patient pulmonary function by removing carbon dioxide from and supplying oxygen to the blood. In contrast to conventional artificial lungs, microfluidic artificial lungs can have a large surface-area-to-blood-volume ratio, biomimetic blood flow paths, and pressure drops compatible with pumpless operation. Initial small-scale microfluidic devices with blood flow rates in the μL/min to mL/min range can exhibit excellent gas transfer efficiencies; however, current manufacturing techniques may not be suitable for scaling up to human applications.

Current artificial lungs used in the clinic typically employ hollow fiber technology. Gas exchange in these devices is achieved by flowing blood around a bundle of hollow fibers through which a sweep gas is supplied. While existing devices based on hollow fiber technology save thousands of lives each year, they have drawbacks that limit further advancements. First, due to their limited gas exchange efficiency, existing devices are typically operated using 100% $O_2$ as the sweep gas in order to support a patient at rest or with minimal activity. Pure $O_2$ is stored in gas cylinders (limiting ambulation) and can potentially create complications associated with hyperoxemia. Further, existing devices have relatively large blood contacting surface areas and blood volumes, both of which contribute to poor long-term hemocompatibility. The majority of the oxygenators that are commercially available have high resistance, therefore a blood pump is required, limiting ambulation and potentially increasing hemolysis and thrombolytic events. The tortuosity of the blood flow path between the hollow fibers enhances mixing and gas exchange but also results in non-uniform flow and varying shear stress throughout the device. High shear areas can cause platelet activation and hemolysis and areas of low shear or stasis promote thrombus formation.

Microfluidic artificial lungs (μALs) as disclosed herein can potentially address many of the drawbacks associated with conventional artificial lungs through increased gas exchange efficiency and biomimetic flow paths. Microfluidic devices have been demonstrated with large surface area to volume (SA/V) ratio resulting in: 1) large gas exchange efficiency; 2) small blood priming volume; 3) the ability to operate using air as the sweep gas; and 4) the option to implement biomimetic flow paths in which blood cells experience pressures, flow velocities, and shear stresses similar to in the natural vasculature.

Despite these advancements, μALs have several challenges to overcome before they can be applied clinically. A major hurdle to the clinical application of μALs is manufacturing. Fabricating μALs can be a multi-step process in which blood and gas channels are formed via standard photolithography and molding methods and then bonded together with a thin membrane sandwiched between. This multi-step process can be suitable for creating small-scale, single gas exchange units that can oxygenate blood with flows in the μL/min to mL/min range. To achieve μALs with sufficient gas exchange area for clinical relevance, individual gas transfer units can be combined in parallel. This can be done by fabricating individual gas transfer units which are then stacked in parallel. However, further scale-up or automated manufacturing of devices in this manner may prove time consuming and problematic. A manufacturing technique to create large area microfluidic artificial lungs does not currently exist.

The following description provides non-limiting examples of manufacturing techniques for creating large-area microfluidic devices such as microfluidic artificial lungs.

Example 1: 3D Printed Microfluidic Artificial Lungs

To date, 3D printing has not been used to create artificial lungs due to the lack of appropriate materials and printing resolution. Recently, high resolution 3D polymer printing has become commercially available but has not been applied to artificial lungs or for printing PDMS. Thus, 3D printing parameters can now be determined for this new application.

Of all the 3D printing technologies, stereolithography (SLA) can print high resolution (<1 μm resolution & <10 μm features) polymer structures using a technique called two photon polymerization and, more recently, using custom high resolution optics and micromirror arrays. SLA was developed by Hull in 1986 and involves UV curing a photosensitive liquid polymer layer by layer to build up a solid 3D object. SLA thus allows for the automated production of complex 3D shapes in virtually any photosensitive polymeric material at low to medium volume throughputs. For example, SLA can be used to produce a SLA 3D printed bioreactor with artificial capillaries with diameters down to 20 µm. Such structures can be formed from a photosensitive polyethylene glycol (PEG) hydrogel and contain liquid flow channels. Up until recently, however, high resolution 3D printing was possible through custom built, complex laboratory systems with small build volumes.

A high resolution SLA 3D printer (i.e., from Nanoscribe (Germany) or Old World Labs (USA) can be used to create the microfluidic artificial lung and test structures of the present invention. The Old World Labs MC-2 has a 100 nm resolution, a 50 nm positional accuracy, a standard 15×15× 15 cm build volume (which can be increased via a custom order), and can print virtually any photosensitive polymer. Photosensitive polydimethylsiloxane (PDMS with photoinitiator) can be used to form the artificial lung and test structures. PDMS has a high permeability to $O_2$ and $CO_2$, favorable biocompatibility properties and has a proven history in commercial artificial lungs and microfluidic artificial lungs. The photosensitive PDMS has achieved a 10 µm feature size or better, and can be further developed for 3D printing parameters for PDMS. Other 3D printers under development may also soon have the required resolution and print size need to print a microfluidic artificial lung.

Figure 9:
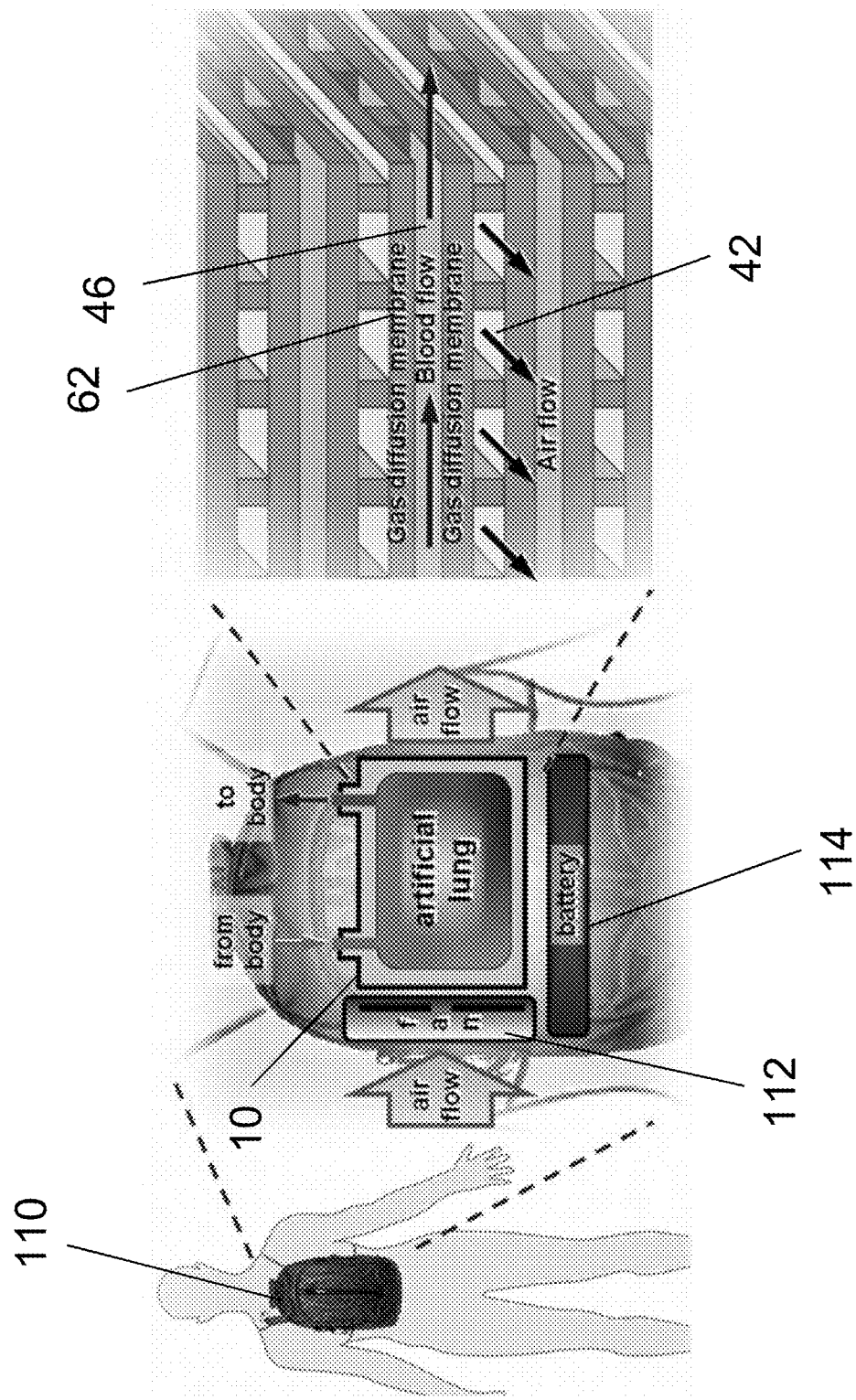
FIG. 9 shows an exemplary wearable artificial lung system, as disclosed herein.
Figure 10:
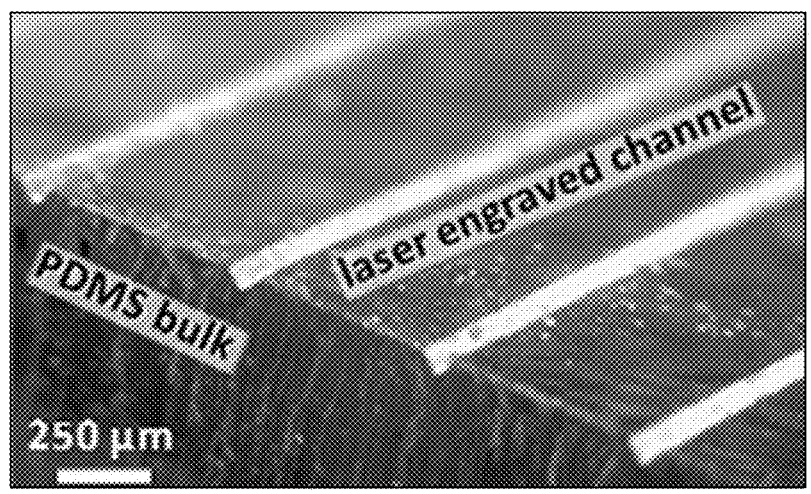
FIG. 10 shows laser engraved channels in PDMS at 8 W, as disclosed herein. The particulate on the surface was removed with an acetone rinse.

Disclosed herein is a wearable arteriovenous (AV) extracorporeal $CO_2$ removal (ECOOR) system for end stage lung disease (ESLD) due to COPD formed using 3D printing. Lung transplantation is the singular effective treatment for ESLD, but the waiting list is long and many patients are not candidates due to age or comorbidities. Patients with end stage COPD suffer terribly. The dyspnea becomes so severe that patients cannot complete a sentence or swallow liquids. Supplemental oxygen helps a little, but the primary problem is high alveolar dead space resulting in $CO_2$ retention requiring increased minute ventilation, exhaustion, wasting, and death. Recent experience has shown that $CO_2$ removal via an artificial lung promptly relieves the symptoms of dyspnea, can improve oxygenation and decrease pulmonary hypertension, and allows rehabilitation. Further research has shown that the amount of blood flow required to remove the metabolically produced $CO_2$ is about 20% of the total cardiac output. $CO_2$ removal between 100 and 250 mL/min has been achieved at blood flows of 1-1.5 L/min and sweep gas flow rates (1-16 L/min) in both commercial artificial lungs (rated flow 4.5 L/min) and custom artificial lungs (rated flow as low as 1.5 L/min). Moreover, $CO_2$ removal is the same in arterial or venous blood and thus an artificial lung for $CO_2$ removal can be driven by arterial pressure eliminating the need for a blood pump. Thus, a wearable AV ECOOR system (with some blood oxygenation) can provide effective palliation to many ELSD patients and allow true ambulation and rehabilitation. One example of such a device is shown in FIG. 9. The diffusion device 10, 200 as disclosed herein can be contained within a small enclosure 110 (e.g., a pack strapped to the hip or torso). A battery pack 114 (or other power source), a light weight air pump 112 (e.g., a fan), and a simple electronic control system for battery charging and pump control (not shown) can also be provided within or associated with the enclosure 110. Blood flow can be driven by AV pressure and vascular access can be selected to permit ambulation (i.e., subclavian artery and vein). Such a system can primarily remove $CO_2$, but also deliver some $O_2$ at 1 L/min blood flow (10-25 mL/min if $SaO_2$ increases from 90 to 100%). This is similar to the oxygen delivery that is delivered to the patient when inhaled $O_2$ is supplemented with an oxygen generator. Some patients with ESLD also have profound hypoxemia in addition to $CO_2$ retention; the hypoxemia is exacerbated during exercise. While these patients may not benefit from the initial system disclosed herein, they can be treated with a venovenous configuration to increase $O_2$ exchange. Briefly, a dual lumen venous catheter can be inserted into the jugular and a small pump (e.g., the Abiomed Impella) can be added to drive blood flow through the device.

It is envisioned that this wearable microfluidic artificial lung can be produced through 3D printing technology. As shown in FIGS. 3A-3D, a 3D printed microfluidic artificial lung disclosed herein features a gas exchange region 221 (middle, FIG. 3A) including a large array of cylindrical artificial capillaries arrayed in an evenly spaced capillary bed (FIGS. 3A & 3D). The sweep gas flows around the outside of each artificial capillary permitting gas exchange from all sides. The inlet and outlet liquid flow networks distribute and collect liquid from the artificial capillaries, respectively. Both distribution networks can be designed to mimic the scaling and branching properties of the natural lung, thereby providing a natural cellular environment in terms of flow velocity, shear stress, and pressure.

Figure 4A:
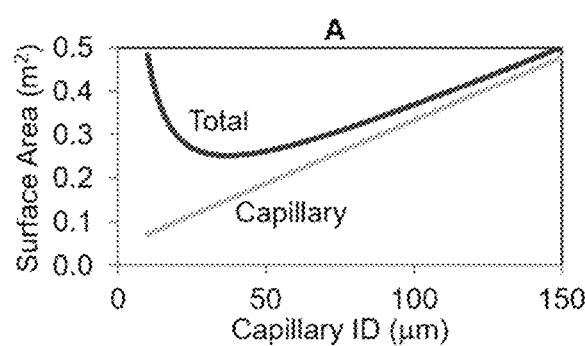
FIG. 4A shows an impact of capillary diameter on total and capillary blood contacting surface area for the design in FIGS. 3A-3D.
Figure 4B:
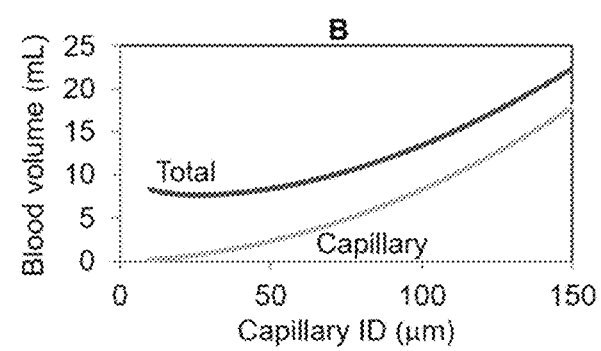
FIG. 4B shows an impact of capillary diameter on total and capillary blood volume.

Previously proven analytical equations (Table 1) were used to model various artificial lung performance metrics (FIGS. 4A-D). For small capillary diameters (inner diameter DCi<25 µm), numerous short capillaries are required to meet the required rated blood flow (1.5 L/min) and capillary shear stress (40 dyn/cm$^2$). Numerous capillaries require a large blood distribution network, resulting in a large total blood contacting surface area and blood volume (FIGS. 4A and 4B). As capillary diameter increases, the length of the capillaries increases to maintain the same shear stress, decreasing the number of required capillaries and thereby decreasing total blood surface area and volume. As capillary diameter increases further (DCi>50 µm in FIG. 4C), gas exchange becomes inefficient due to increased diffusion distance. This results in a larger required gas exchange surface area and larger blood volume. Due to these phenomena, surface area (FIG. 4A) and blood volume (FIG. 4B) have local minima at artificial capillary inner diameters (DCi) of 37 µm and 26 µm, respectively. For any blood contacting device, it is desirable to minimize the blood contacting surface area and the blood volume ("priming volume") in order to minimize the foreign body response and improve patient outcomes.

For clinical application, the device must be able to operate without a blood pump using peripheral arteriovenous pressure. The difference between the mean peripheral arterial and venous pressures in normal adults is approximately 80 mmHg. Allowing approximately 20 mmHg for tubing and cannula, artificial lung blood side pressure should be less than 60 mmHg at its rated flow. Blood side pressure drop (FIG. 4C) is less than 60 mmHg for the values of capillary inner diameter (DCi).

Figure 4C:
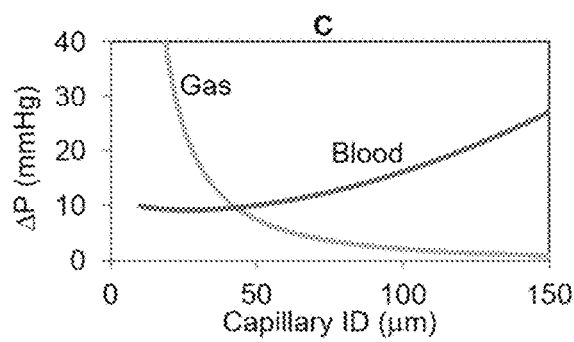
FIG. 4C shows an impact of capillary diameter on pressure drop on the gas and blood sides of the device.
Figure 4D:
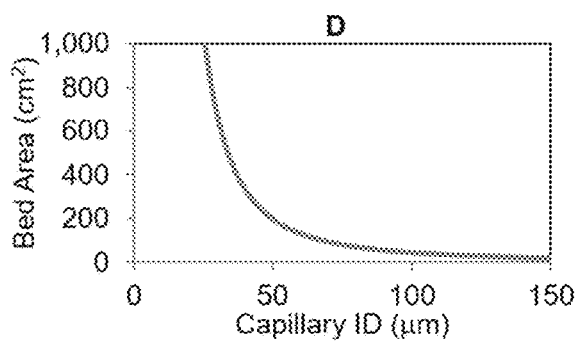
FIG. 4D shows an impact of capillary diameter on the bed or printing area. Rated flow ($Q_R$—the maximum blood flow rate at which an inlet blood saturation of 70% can be oxygenated to an outlet oxygen saturation of 95% was fixed at 1.5 L/min; capillary shear stress was fixed at 40 dyn/cm$^2$; the sweep gas was pure oxygen at 16 L/min; capillary wall thickness ($\delta_M$) was 20 μm; distance between adjacent capillaries was 50 μm; membrane material was polydimethyl siloxane (PDMS).

To avoid pressure driven gas flow across the membrane (and thus, bubble formation in blood), the maximum gas side pressure in an artificial lung should not exceed its minimum blood side pressure. The minimum blood side pressure is venous pressure plus the pressure drop of the tubing or approximately 20 mmHg. This value sets the upper bound for the gas side pressure. Capillary diameters greater than 28 µm result in a gas-side pressure drop less than 20 mmHg (FIG. 4C).

To minimize platelet activation and cell lysis, shear stress in an artificial lung should be similar to that seen in the natural vasculature. In the human vascular system, shear stress ranges between 10 and 70 dyn/cm$^2$ in arteries and between 1 and 6 dyn/cm$^2$ in veins. For this design, capillary shear stress was fixed at mean arterial shear or 40 dyn/cm$^2$. This combination of capillary shear stress and pressure drop (<60 mmHg) ensure that blood trauma factors are much less than that required for hemolysis.

Finally, the limitations of the 3D printer must be taken into account. Although the OWL MC-2 can be custom ordered with a larger build volume, a standard system with a 15×15×15 cm build volume was used. After taking into account the structural manifold of this device, the area remaining for the capillary bed is 13.5×13.5 or 182 cm2. DCi>52 µm in FIG. 4D results in a capillary bed area less than 182 cm$^2$. Other 3D printing technologies have similar limitations to their printing area.

TABLE 2

Physical dimensions of the cylindrical, 3D printed, fluidic test structures.

| Inner diameter (µm) | Wall thickness (µm) |
|---|---|
| 10, 25, 50, 75, 100 | 5, 10, 20, 30, 40 |

Surface roughness and mechanical robustness (burst pressure) measurements can be repeated in triplicate and each experiment can be repeated with four (4) test structures. Measurements can be converted to means and standard deviations and compared using a student t-test (p-value=0.05).

TABLE 1

Analytical equations used for the design of the 3D printed artificial lung.

$$Q_R = \frac{A_{GE}}{S_{B,O2} \cdot R_{D,O2} \cdot \ln\left(\frac{PO2_{B,i} - PO2_G}{PO2_{B,o} - PO2_G}\right)} \quad (1) \qquad R_{D,O2} = \frac{\delta_M}{P_{M,O2}} + \frac{D_{Ci}/4}{S_{B,O2} \cdot D_{B,O2}} \quad (2) \qquad \Delta P_C = \frac{128 \cdot \mu_B \cdot L_C}{n \cdot \pi \cdot D_{Ci}^4} Q_R \quad (3)$$

$$\Delta P_{GAS} = \frac{150 \cdot \mu_G \cdot L}{D_P^2 \cdot W \cdot H} \cdot \frac{(1-\epsilon)^2}{\epsilon^3} Q_G \quad (4) \qquad \tau_W = \frac{\Delta P_C \cdot D_{Ci}}{4 \cdot L_C} \quad (5) \qquad r_{parent}^3 = \Sigma r_{daughter}^3 \quad (6)$$

Notes:
$Q_R$ is rated blood flow; $Q_G$ is gas flow; $A_{GE}$ is gas exchange surface area; $S_{B,O2}$ and $D_{B,O2}$ are the effective oxygen solubility and diffusivity in blood; $R_{D,O2}$ is resistance to oxygen diffusion; $PO2_{B,i}$, $PO2_{B,o}$ and $PO2_G$ are the partial pressure of oxygen in the blood inlet, blood outlet, and sweep gas, respectively; $\delta_M$ is the thickness of the gas diffusion membrane; $P_{M,O2}$ is the permeability of the membrane to oxygen; $D_{Ci}$ is capillary inner diameter; $\Delta P_C$ is capillary pressure drop; $\mu_B$ and $\mu_G$ are the viscosity of blood and the sweep gas; $L_C$ is capillary length; n is the number of capillaries; L, H, and W are length, height, and width in the direction of flow; $\Delta P_{GAS}$ is the gas side pressure drop (using the Blake-Kozeny equation for flow through a porous media); $D_P$ is the effective particle diameter in the porous media, $\epsilon$ is the media porosity; $\tau w$ is wall shear stress; $r_{parent}$ and $r_{daughter}$ are the radii of parent and daughter vessels in a biomimetic branching system.

To minimize blood contacting surface area and blood volume given the constraints above, DCi was set to 52 µm resulting in a total blood contacting surface area of 0.25 m$^2$, a total blood volume of 8.3 mL, a blood side pressure drop of 10 mmHg (at a rated blood flow of 1.5 L/min), a gas side pressure drop of 7.5 mmHg (at a gas flow of 16 L/min), and a total device size of 15×15×15 cm (including fluidic distribution and structural manifolding). The device described herein can exchange 30 mL/min (air sweep gas) to 70 mL/min (O$_2$ sweep gas) of O$_2$ in a VV configuration or 10 mL/min (air sweep gas) to 25 mL/min (O$_2$ sweep gas) of O$_2$ in an AV configuration. In either configuration, the device can remove 100-250 mL/min of CO$_2$ (sweep gas of 1-16 L/min) as demonstrated in previous devices with similar rated blood flows. For comparison, if the state of-the-art Novalung iLA Membrane Ventilator were scaled down to a rated flow of 1.5 L/min, it would have a blood contacting surface area of 0.45 m$^2$ and a total blood volume of 58 mL. Cylindrical flow conduits of various diameter and wall thickness (Table 2) can be designed in 3D CAD software and then printed. A previously-developed photosensitive PDMS can be configured for use in the high resolution MC-2 polymer 3D printing system or other high resolution 3D printers. PDMS to photoinitiator ratio and exposure dose can be modified to achieve suitable resolution and printing speed. The MC-2 and configured photosensitive PDMS can then be used to 3D print the test flow conduits (Table 2). Printed flow conduits can be inspected for continuity, surface roughness, and replication of drawn features and tested in the laboratory for mechanical robustness (leaks and burst pressure). Minimum diameter and wall thickness can be determined based on target application pressures (250 mmHg max).

The methods and systems described herein can result in: 1) a photosensitive PDMS formulation configured for use in the 3D printing system; 2) a 3D printing recipe for photosensitive PDMS (exposure dose, printing speed, etc.); and 3) minimum flow conduit diameter and wall thickness for use in the 3D printed artificial lung. The methods and systems described herein can result in a printed cylindrical, PDMS, with fluidic conduits having inner diameters and wall thicknesses of less than 50 µm each. The polymer formulation and printing parameters can be adjusted until success is achieved.

Configured parameters can be used to create 3D printed, microfluidic artificial lungs meeting the above specifications. Blood flow networks can be designed to mimic the pressures, flow velocities, and shear stress in the natural lung. In contrast to current microfluidic artificial lungs, each artificial capillary of the disclosed devices can be completely surrounded by the sweep gas, thereby increasing gas exchange efficiency relative to previous devices. Computational Fluid Dynamics (CFD; SolidWorks) can be used to visualize flow and shear distribution throughout the blood flow network, to verify pressure drop, and to configure the overall design before printing. The final 3D CAD design can be printed using the parameters developed above. A single device can be printed and tested before proceeding with additional printing. Testing can occur in the laboratory with saline, whole blood, and oxygen or air sweep gas to validate pressure drops and gas exchange as functions of flow rates.

The methods and systems disclosed herein can result in advancements in the ability to simply and easily manufacture large area microfluidic artificial lungs, thereby accelerating the timeframe to clinical application of these devices. The methods and systems disclosed herein can be directed to a 3D printed artificial lung for large animal testing that can be subsequently translated to the clinical setting through its application in systems targeted at acute lung support for pulmonary rehabilitation. The resulting 3D printed PDMS flow networks can have uses in, for example, but not limited to, bioreactors, dialysis, and filtration processes.

Example 2: Rolled-Membrane Microfluidic Artificial Lung Designed for Large-Area Manufacturing with Biomimetic Blood Flow Networks Described herein is a new manufacturing technology for a microfluidic artificial lung (μAL) in which the structure is assembled via a continuous "rolling" and bonding procedure from a single, patterned layer of polydimethyl siloxane (PDMS). The patterned PDMS can be rolled around a cylindrical substrate. In this rolling process, the blood and gas layers can be automatically separated by a PDMS membrane. By patterning alternating blood and gas layers on a single flat template, multiple gas exchange units can be stacked on top of each other in a one-step rolling process. Further, this method can provide an area for gas exchange on both the top and bottom of the artificial capillaries between two gas channels. In contrast, existing designs allow for gas transfer through only one surface of the capillary.

The disclosed method can be demonstrated in a small-scale four-layer device, but is expected to easily scale to larger area devices. Exemplary devices can have a biomimetic branching blood flow network, 10 μm tall artificial capillaries, and a 66 μm thick gas transfer membrane. Gas transfer efficiency in blood was evaluated over a range of blood flow rates (0.1-1.25 mL/min) for two different sweep gases (pure $O_2$, atmospheric air). The achieved gas transfer data closely followed predicted theoretical values for oxygenation and $CO_2$ removal, while pressure drop was marginally higher than predicted. Although designed for microfluidic artificial lungs, the technique described herein can result in the first manufacturing method capable of simply and easily creating large area microfluidic devices in PDMS.

The successful fabrication of cylindrical μALs can be demonstrated using the method. The pressure drop across these devices was recorded along with the gas transfer efficiency for oxygenation and $CO_2$ removal. Additionally, the performance of these devices was compared to a clinically used artificial lung and other microfluidic artificial lungs. Finally, it is further contemplated that the disclosed methods can be used to create large area microfluidic devices in PDMS.

Experimental Methods

Device design overview: A rolled microfluidic device can be designed to have a four-layer structure (blood layer/membrane/air layer/capping layer). Deoxygenated blood entering the device can be distributed to 5450 artificial capillaries (10 μm height, 40 μm width, 1014 μm long), and sweep gas (pure $O_2$ or air) can be fed through a bank of 100 μm high channels. The priming volume of the device (not including the tubing circuit) can be 27 μL of blood. The blood and gas channels can be separated by a 66 μm thick PDMS membrane. After the gas channel layer is wrapped around the substrate, the tops of the gas channels can be open to the outside; thus, the capping layer can be included to fully enclose the gas channels. As blood flows through the device, $O_2$ in the sweep gas can diffuse across the PDMS membrane and into the oxygen-depleted blood via a partial pressure gradient. Simultaneously, accumulated $CO_2$ in the blood can diffuse across the membrane and exit with the sweep gas. The blood flow rate, sweep gas composition, and sweep gas flow rate can be varied to affect the $O_2/CO_2$ content of the blood exiting the device.

The blood flow path was designed using scaling relationships of the natural lung in order to ensure physiologic shear stress throughout and to control pressure drop. The relative diameters of the parent and daughter channels were designed to follow Murray's law, which states that in a flow network which minimizes work, the cube of the radius of a parent vessel equals the sum of the cubes of the radii of the daughter vessels. This manufacturing method is different in that the device is formed by rolling a cylindrical substrate over a coated template, thereby stacking the four layers (blood/membrane/air/cap). Unlike early artificial lung work, in which a silicone sheet was rolled around a cylindrical substrate, the disclosed microfluidic devices: (a) integrate small diameter microfluidic channels, (b) implement a bio-inspired flow path, resulting in a pressure drop compatible with pumpless operation, (c) form the device completely from PDMS, and (d) permanently bond each layer together. FIGS. 5A-B show a schematic of the fabrication of the rolled devices and illustrate the basic procedure used for fabrication. The lengths of the blood and gas areas can be equal to the circumference of the cylindrical substrate, so that each layer (blood/gas) constitutes one revolution of the substrate as it is rolled. The membrane thickness between the blood/gas layers, then, can correspond to the difference between the overall thickness of the PDMS sheet cast over the template and the height of the gas channels.

Device fabrication. Construction of molds and PDMS layers can follow the methods disclosed herein. Briefly, molds were formed on 6" silicon wafer substrates using negative photoresist, (i.e., MicroChem SU-8) a spin coater (i.e., Specialty Coating Systems™ Spincoat G3P-12 spin coater), and an exposure unit (i.e., Kinsten KVB-30D UV exposure unit). FIG. 5A shows a schematic of the patterning of the silicon wafers with the blood channel, gas channel, and cap ("capping") layer templates. Sylgard® 184 silicone elastomer base and curing agent (10:1, Dow Corning) (PDMS) were mixed, degassed, spun to a thickness of 166 and cured at 80° C. for 45 minutes.

Figure 6A:
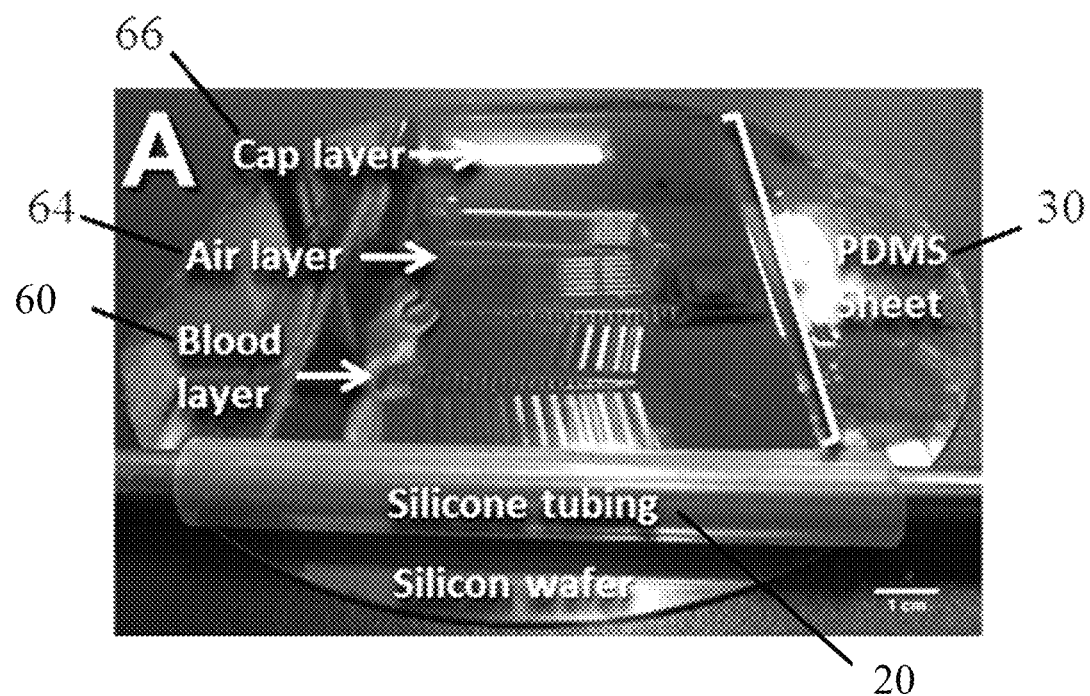
FIGS. 6A-D show images depicting the beginning of the rolling process, the rolled device and a cross-section of the rolled device.
Figure 6B:
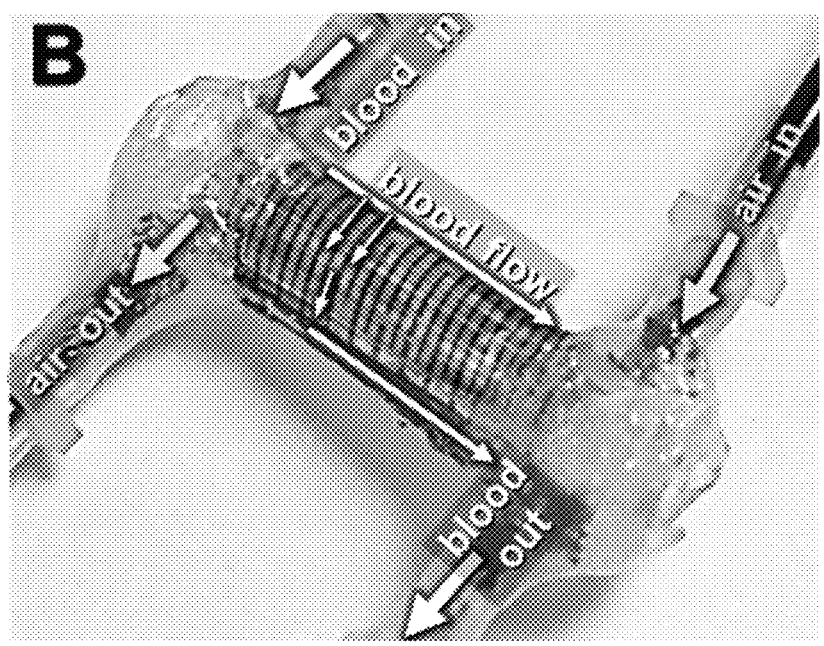
Figure 6C:
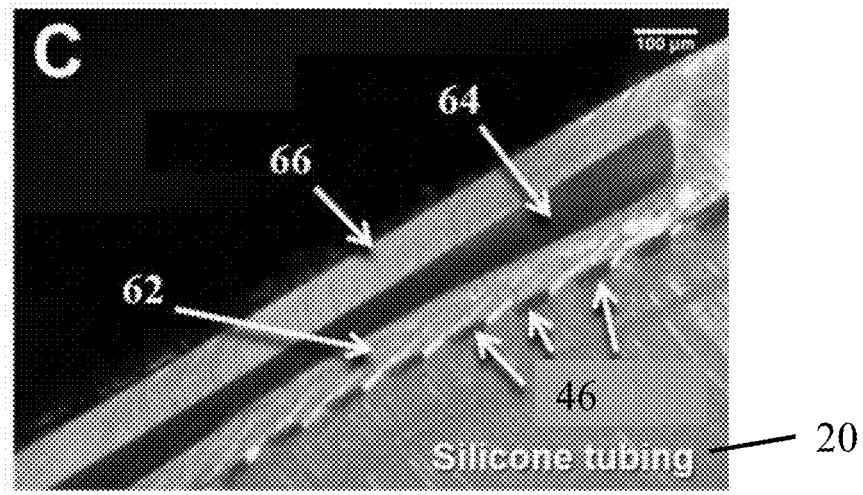

FIGS. 6A-C show device fabrication, with FIG. 6A showing an image of the beginning of the rolling process in which the silicone tubing substrate has been bonded to the edge of the PDMS sheet. FIG. 6B shows an image of a rolled device with dyed water flowing through to illustrate the blood and gas flow paths. FIG. 6C shows an image of the cross-section of a rolled device as disclosed herein.

The rounded sides of the now patterned PDMS were trimmed to produce a rectangular sheet (FIG. 6A). An approximately 3" length of silicone tubing (Masterflex® 96410-18) was used as the inner support structure of the rolled device. The support tubing and patterned PDMS sheet were activated with $O_2$ plasma (900 mTorr, 25 W) for 25 seconds and the tubing was immediately contacted to the edge of the PDMS (FIG. 6A). The PDMS and tubing were treated with $O_2$ plasma again and the tubing was slowly rolled by hand approximately a ½ turn. For this study, devices were rolled by hand; however, to reduce variation between devices and for future scale up, it is contemplated that this process can be automated using conventional motors, actuators, and feedback/processor control. This process can be repeated until the PDMS is completely rolled around the support tubing. Inlet and outlet holes were cut using a 2 mm biopsy punch. Silicone tubing inlet/outlet ports were bonded over these holes using RTV silicone epoxy (Dow Corning) to direct flow into the microchannels.

To confirm that the rolling procedure itself does not cause significant distortion of the microfluidic features, planar devices were fabricated using the same molds used to fabricate rolled devices. To achieve this, the silicon wafer mold was used to prepare two separate patterned PDMS substrates/layers, one for blood flow and one for gas flow. A membrane was spun to the same thickness achieved by the rolled device on a flat substrate and was bonded between the blood and gas flow layers. Pressure drop versus blood flow for the rolled device and planar device were then measured and compared.

Gas exchange model. A mathematical model can be used to predict the gas exchange performance of the rolled device. The model can be used to predict the partial pressures of $O_2$ ($pO_2$) and $CO_2$ ($pCO_2$) in the blood at the outlet of the device based on device parameters and inlet blood gas measurements. The equations below outline the $pO_2$ calculation, and analogous equations are used to calculate $pCO_2$.

$$pO_{2B,o} = pO_{2G} + (pO_{2B,i} - pO_{2G})e^{-\frac{A}{QS_{B,O2}R_{D,O2}}} \quad (7)$$

The $pO_2$ in blood at the outlet of artificial capillaries ($pO_{2B,o}$) is a function of the $pO_2$ in the sweep gas ($pO_{2G}$), the $pO_2$ in the entering blood ($pO_{2B,i}$), the gas exchange surface area (A), the blood flow rate (Q), the effective solubility of $O_2$ in the blood ($S_{B,O2}$), and the total resistance to $O_2$ diffusion ($R_{D,O2}$).

$$R_{D,O2} = \frac{\delta_M}{P_{M,O2}} + \frac{\delta_B}{S_{B,O2}D_{B,O2}} \quad (8)$$

The total resistance to oxygen diffusion is a function of the membrane thickness ($\delta_M$), the membrane permeability to oxygen ($P_{M,O2}$), the blood side fluidic boundary layer ($\delta_B$, estimated as half of artificial capillary height), and the effective diffusivity $O_2$ in blood ($D_{B,O2}$). With the calculated $pO_{2B,o}$, the fractional $O_2$ saturation ($SO_2$) was calculated using the Hill equation (9), where $PO_2$ is the partial pressure of oxygen in blood, $P_{50}$ is the partial pressure of oxygen where the blood is 50% saturated, and n is the Hill coefficient (which for normal human blood is 2.7). As used here, $P_{50}$ and n are estimated so that the coefficients more accurately represent experimental conditions. This is done by minimizing root mean square error between the experimentally measured values of $SO_2$ and the values calculated using the Hill equation. Here, $P_{50}$=32.2 and n=2.9.

$$SO_2 = \frac{(PO_2/P_{50})^n}{1+(PO_2/P_{50})^n} \quad (9)$$

Pressure drop and shear stress calculation. The following equation can be used to predict the blood-side pressure drop across each channel in the rolled device.

$$\Delta P = \frac{12\mu L}{HW^3\left(1-\frac{0.63 \cdot H}{W}\right)}Q \quad (10)$$

Pressure drop in rectangular channels is a function of the channel height (H), width (W), and length (L), as well as blood viscosity and blood flow rate. To arrive at a value for the entire rolled device, each channel was represented as a resistance (Q/ΔP) which was then combined into a single value using Kirchhoff's rules. Blood viscosity was estimated using measured hematocrit values of blood used for in vitro testing. This value was calculated using the equation below where $\mu_P$ is bovine plasma viscosity (measured previously to be 1.72 cP) and H is the measured hematocrit.

$$\mu=\mu_P\{1+0.025H+(7.35*10^{-4})H^2\} \quad (2)$$

Shear stress at the bottom of the channels and at the midpoint of the width can then be approximated.

$$\tau = \eta\frac{\Phi}{q}\left\{\sum_{n=0}^{\infty}\frac{(-1)^n b\pi}{(2n+1)^2}\left(\frac{2}{\pi}\right)^3\tanh\left[(2n+1)\frac{\pi h}{2b}\right]\right\} \quad (12)$$

$$q = \frac{4}{3}hb^3 - 8b^4\left(\frac{2}{\pi}\right)^5\sum_{n=0}^{\infty}\frac{1}{(2n+1)^5}\tanh\left[\frac{(2n+1)\pi h}{2b}\right] \quad (13)$$

In equations 12 and 13, η is the dynamic viscosity (dyn*s/cm$^2$), Φ is the flow rate (cm$^3$/s), b is ½ the channel width (W), and h is ½ the channel height (H).

In vitro testing. Devices were tested to confirm successful bonding and membrane integrity by filling the blood and gas sides of the device with dyed DI water at 0.1 mL/min (FIG. 6B) using a programmable syringe pump (i.e., Harvard Apparatus). Devices were rinsed with DI water and dried before further testing. Anticoagulated (16% v/v citrate phosphate dextrose) bovine whole blood was purchased (Lampire) and stored for one day at 4° C. to permit the cells to metabolize the oxygen into $CO_2$, thereby providing venous blood gas levels. Fabricated devices were connected to the blood and gas sources via silicone tubing and placed in a 37° C. water bath. Gas was supplied via either a pure $O_2$ cylinder or compressed air and a gas flow controller (i.e., Omega, model FMA5502) was used to supply gas to the device at a flow rate of 1 mL/min. Blood was supplied to the blood-side inlet of the device at varied flow rates (0.1-1.25 mL/min) using a programmable syringe pump. Pressure sensors (PC series, Honeywell) were used to monitor blood and gas pressures on the inlet and outlet of the device. At each flow rate, a blood sample was taken by filling a small diameter vial and pipetting from the bottom of the blood column. Blood was analyzed with an Abbott Point of Care (APOC) iSTAT Handheld Blood Analyzer. APOC EG6+ Cartridges were used to provide relevant blood gas information including $pCO_2$, $pO_2$, $SO_2$, hematocrit and hemoglobin levels.

Results and Discussion

Device fabrication. A successfully fabricated device is shown in FIG. 6B, in which dyed water is being flowed through to confirm the flow paths for the blood and sweep gas. Upon confirming gross functionality, successfully fabricated devices (n=6) were used for in vitro testing. In determining the best method for fabrication, some commonly experienced issues arose which are highlighted below.

Unwanted adhesion between the PDMS and template can cause the PDMS to rip when attempting to roll around the substrate. This is prevented by pre-treating wafers in a vacuum desiccator with a drop of (Tridecafluoro-1,1,2,2-tetrahydrooctyl)-1-trichlorosilane for at least 1 hour prior to coating wafers with PDMS. Partial or incomplete bonding was another common problem which caused device failure. When testing with dyed water, these devices have substantial leakage from the intended blood/gas flow paths where bonding between layers was not complete. Partial bonding can occur if the substrate is rolled more than ½ turn after activating, as the surfaces which are activated will bond. Partial bonding can be avoided by rolling the substrate at most ½ turn after each successive $O_2$ plasma treatment. Finally, proper alignment of the substrate with the PDMS sheet upon initial bonding was important for successful fabrication. Misalignment of the substrate causes the inlet/outlet ports to be misaligned when fully rolled. Attempting to correct the alignment during the rolling causes "wrinkles" to occur, in which excess PDMS is not completely and continuously bonded to the substrate. Proper alignment can be difficult to achieve manually.

Devices were rolled by hand, which introduces opportunity for variation between devices and within each device (due to stretching of PDMS, wrinkling, etc.). The process is being automated, which will reduce the amount of variation between and within device and will increase the repeatability of the fabrication procedure.

The number of layers that comprise the device is limited by the length of the mold from which the PDMS is rolled. As described herein, spin coating is used to deposit desired thicknesses of photoresist when making the device mold, and also when coating the completed mold with PDMS. In vitro performance: pure $O_2$ sweep gas. Since the $O_2$ transfer is driven by a partial pressure gradient, the most efficient $O_2$ transfer into blood occurs using pure $O_2$ as the sweep gas.

FIGS. 7A-D show the gas transfer performance of rolled membrane devices (n=6) employing $O_2$ (A, C) or air (B, D) as the sweep gas. FIG. 7A shows the $SO_2$ of blood exiting devices using pure $O_2$ sweep gas (n=6). Normal arterial $SO_2$ levels in healthy adults range between 95-100%, with values under 90% being considered low. The blood flow capacity of artificial lungs is typically characterized by the "rated flow", and is defined as the maximum blood flow rate at which the $O_2$ content of entering venous blood (70% $SO_2$) will be raised to 95% $SO_2$. In other words, an artificial lung operating above its rated flow will result in blood exiting at <95% $SO_2$. The theoretical rated flow of the device with $O_2$ as the sweep gas is 1.4 mL/min (calculated using Eqn. 7 and the Hill Equation). Experimentally, the outlet oxygen saturation was 95% for a flow rate of 0.5 mL/min (n=3, FIG. 7A). This value is less than the theoretical rated flow because theoretical rated flow is calculated using a specific set of blood conditions, which differ from the experimental conditions. Inlet blood conditions were measured before each experiment, and those values were used to determine the theoretical values included in FIGS. 7A-D (dot-dash lines). For instance, the oxygen saturation of the inlet blood was below the theoretical inlet $O_2$ content used in calculating theoretical rated flow (70%). The mathematical model output plotted on FIG. 7A was calculated using the experimentally measured inlet blood $O_2$ content and hematocrit, and agrees well with experimental data particularly at flow rates ≤1 mL/min.

In vitro performance: air sweep gas. Using air as the sweep gas is advantageous because it removes the need to transport a compressed $O_2$ cylinder, improving device portability. The theoretical rated flow for a single gas exchange unit using air as the sweep gas is approximately 0.20 mL/min with air as the sweep gas. Experimentally, the device provided outlet blood $SO_2$ above 95% up to a flow rate of about 0.2 mL/min (n=6). The experimental outlet $SO_2$% closely agrees with the mathematical model when the actual inlet blood $SO_2$% is used in the calculation (FIG. 7B).

$CO_2$ Removal. FIGS. 7A-D also contains the $CO_2$ removal data for devices using either $O_2$ or air sweep gas (n=6). The normal range of the $pCO_2$ in arterial blood is 38-42 mmHg. For blood flows less than 0.5 mL/min, blood exiting the devices was consistently within or below this normal range. The outlet $pCO_2$ increases with blood flow rate, resulting from a smaller residence time within the gas exchange unit. The $CO_2$ removal is approximately the same when using either $O_2$ or air as the sweep gases, as the difference in $CO_2$ content of either incoming sweep gas is negligible.

Pressure drop and shear stress in device. Theoretical pressure drop through the rolled device is calculated using Equation (10), and is dependent on channel geometry, flow rate, and blood viscosity. The blood viscosity is estimated using measured values of hematocrit for the blood used in the experiments (Equation 11). The average hematocrit of inlet blood used in this experiment was measured as 24.2±3.9 (average±standard deviation), giving an estimated blood viscosity of 2.04 cP.

Figure 8:
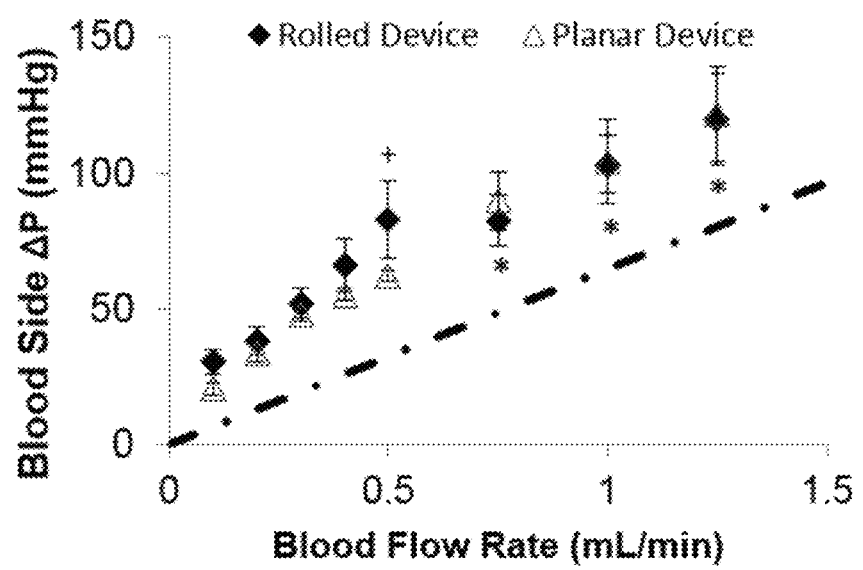
FIG. 8 shows the measured (data points) and theoretical (dash-dot line) blood side pressure drop of rolled membrane devices (diamonds, n=6, HCT=24.3±3.9), and planar devices with the same blood flow path (triangles, n=2, HCT=17), at various blood flow rates. Error bars represent standard error of measured values, +n=5 *n=3).

FIG. 8 provides the measured and theoretical (dash-dot line) blood side pressure drop of rolled membrane devices (diamonds, n=6, HCT=24.3±3.9), and planar devices (triangles, n=2, HCT=17), at various blood flow rates. Error bars represent standard error of measured values, +n=5 *n=3). FIG. 8 gives the average pressure drop across the blood side of the device with anticoagulated bovine blood as the working fluid. The natural lung operates with a pressure drop of roughly 10 mmHg. Most Extracorporeal Membrane Oxygenation (ECMO) circuits can operate safely to an upper limit of roughly 300 mmHg; however, higher pressures (>≈80 mmHg) require the use of a blood pump. Pressure drop increased linearly with flow rate over the range tested (0.1-1.25 mL/min) and was roughly 2-3.5 times higher than predicted theoretical values (n=6). A similarly designed blood channel layout also resulted in pressure drops roughly twice as high as the calculated values. The difference between theoretical and experimental values is thought to be due to the fact that theoretical calculations do not take into account changes in blood flow direction at the inlet/outlet and bifurcations, the hydrophobic nature of the channels, and possibly differences in calculated and experimental viscosity. The pressure drop observed through the planar device agreed well with that of the rolled device, indicating that the rolled fabrication method itself did not result in a significant increase in vascular resistance compared to the stacking method.

Normal physiological values for shear stress in capillaries and arterioles are about 53 dyne/$cm^2$ and 43 dyne/$cm^2$, respectively. Using the estimated blood viscosity, the shear stress in the device can be estimated using Equations (12) and (13). The estimated shear stress in the vessels in the device was comparable to physiological values, ranging from 2.4-11.1 dyn/$cm^2$ at 0.1 mL/min and from 11.8-55.4 dyn/$cm^2$ at the device's rated flow of 0.5 mL/min. At the highest flow rate tested (1.25 mL/min), the shear stress in the capillaries is estimated to be 138.5 dyn/$cm^2$, which is higher than typical physiological shear. However, inlet (24.2±3.9%) and outlet (26.1±4.9%) blood hematocrit measurements did not provide any indication of significant hemolysis due to increased shear.

Comparison to other devices. Table 3 compares the gas exchange performance of the rolled devices with several recently published μALs as well as the commercially available Maquet Quadrox-i Neonatal oxygenator. Here, both the gas transfer rate ($O_2$ or $CO_2$) and blood flow rate is normalized to the effective gas transfer area, in order to provide a comparison of performance in these devices. At the same normalized blood flow, the gas exchange efficiency of the rolled device using $O_2$ sweep gas is higher than the commercially available device. At the same normalized blood flow using air sweep gas, the rolled device is slightly less efficient than the commercial device (which uses $O_2$ sweep gas).

The rolled device displays oxygen exchange efficiencies comparable to other recently reported μALs using either $O_2$ or air sweep gas.

Device scale-up. Future microfluidic artificial lungs will be composed of multiple gas exchange units rather than the single unit design used here. This stacking of gas exchange units in parallel will likely be necessary for any μAL. The rated flow will increase as the number of units stacked together increases. As the units are stacked in parallel, blood side pressure drop should not be significantly impacted.

One benefit to the rolled design disclosed herein is that the increase in the rated flow will be greater than simply a proportional increase expected by adding more units in parallel. With this rolled design, each interior blood channel will be situated between two gas channels. This allows gas diffusion from two sides of the artificial capillaries, thereby providing more efficient gas exchange than diffusion in one direction. An increase in gas exchange can be estimated by calculating a diffusional resistance for the top and bottom membranes and combining using parallel resistances: $R=R1 \cdot R2/(R1+R2)$. For the rolled device disclosed herein, each intermediate blood channel would have access to two gas exchange membranes—having approximately 66 and 100 μm thickness, respectively. The two-directional diffusion in this case is estimated to increase the rated flow of a single unit by roughly 80%, which would almost halve the amount of gas exchange units required to reach the same rated flow.

The natural lung operates with a pressure drop of roughly 10 mmHg. The requirements of the artificial lung can vary depending on the application, the type of vascular access (arteriovenous, venovenous, etc.), and on the needs of the patient. Assuming arteriovenous access, the device would need to be designed to have a pressure drop below 80 mmHg in order to provide pumpless operation. For pumpless operation, the entire extracorporeal circuit (cannula, tubing, artificial lung, etc.) would need to operate using physiologic pressures. For peripheral arterio-venous access, available pressure for the entire extracorporeal circuit is limited to approximately 80 mmHg in a normal adult. The pressure available to the artificial lung will be somewhat less than approximately 80 mmHg. As examples of clinical relevance, two commercially-available artificial lungs with a history of use in pumpless configurations have pressure drops of 5.5 mmHg (Novalung iLA) and 18 mmHg (Maquet Quadrox-i Adult) at a blood flow of 2 L/min. Physiological shear stresses range between 10-70 dyne/cm² in arteries and 1-6 dyne/cm² in veins. The scaled-up device is designed to have shear stresses within these ranges to mimic the natural vasculature as closely as possible.

An important consideration with μAL is the scale-up required to support clinically relevant blood flow rates. Comparison to currently used artificial lungs can provide insight into the requirements of the scaled-up microfluidic artificial lung. As an estimate for the minimum rated flow useful for human application, the Maquet Quadrox-i Neonatal oxygenator has a priming volume of 38 mL, uses $O_2$ sweep gas, and operates at flow rates as low as 0.2 L/min and as high as 1.5 L/min. At 1.5 L/min, the device provides roughly 90 mL/min of $O_2$ exchange and 73 mL/min of $CO_2$ exchange at a pressure drop of about 65 mmHg. At 0.2 L/min, the device provides roughly 15 mL/min of $O_2$ exchange and 10 mL/min of $CO_2$ exchange at a pressure drop of about 8 mmHg. A larger device, the Maquet Quadrox-i Small Adult oxygenator, has a recommended blood flow rating of 0.5-5 L/min has a priming volume of 215 mL. A Maquet Quadrox-i Small Adult oxygenator operating at 0.5 mL/min of blood flow provides roughly 30 mL/min of $O_2$ transfer and 55 mL/min of $CO_2$ transfer at a pressure drop of about 10 mmHg.

As the rolled device is scaled to include more gas exchange layers, each subsequent layer will become longer to account for the corresponding increase and device diameter. As device diameter increases and subsequent layers get longer, each gas exchange unit will provide roughly a proportional increase in gas exchange surface area (and also priming volume per layer). Also, increasing the length of the device will increase the gas exchange surface area per layer. Assuming a scaled up device (with twice the width of the device presented herein) has a rated blood flow of 1 mL/min using $O_2$ as the sweep gas for the first layer, roughly 219 gas exchange units would be required to support 1.5 L/min of blood flow. The device would be cylindrical with a length of 6" (15.2 cm) and a diameter of 5.6" (14.2 cm), and would have a priming volume of about 41 mL. Using air as the sweep gas, a rolled device with a rated flow of 1.5 L/min would have 355 gas exchange units, a diameter of 8.8" (22.4 cm), and a priming volume of 71 mL. The theoretical rolled device would provide 102 mL/min $O_2$ transfer and 201 mL/min of $CO_2$ transfer, based on the measured gas exchange efficiency (Table 3) and the gas exchange area of a scaled-up device. The design of multi-layer devices can be optimized, and demonstrates the potential afforded by the rolled approach. Optimization parameters of the channel design to produce the devices described herein can include, for example, but not limited to minimized size, priming volumes, and pressure drops while maximizing rated flows.

TABLE 3

Comparison of recently published performance data for microfluidic artificial lungs. Data is from other reported works, or estimated from reported values. H is artificial capillary height. $\delta_M$ is membrane thickness. SAV is the surface-area-to-blood-volume ratio in the effective gas exchange area. SAGE is the percent of blood contacting surface area that contributes to gas exchange. Values in the table represent the maximum values for gas exchange. Values are calculated for the membrane area that is effectively contributing to gas exchange. Numbers in parenthesis include both the gas exchange and blood distribution regions to give total device values, when applicable.

| Source | H (μm) | $\delta_M$ (μm) | SAV (cm⁻¹) | SAGE % | $O_2$ Exchange mL $O_2 \cdot$ min⁻¹ · m² | $CO_2$ Exchange mL $CO_2 \cdot$ min⁻¹ · m² | Blood Flow mL · min⁻¹ · m² | Sweep Gas |
|---|---|---|---|---|---|---|---|---|
| Rolled Device | 10 | 66 | 830 (158) | 46 (18) | 153 (66) | 303 (130) | 2.64 | $O_2$ |
|  | 10 | 66 | 830 (158) | 46 (18) | 102 (44) | 296 (127) | 2.64 | Air |
| Hoganson 2011 | 100 | 9 | 100 | 25 | (41) | (191) | (9.1) | $O_2$ |

TABLE 3-continued

Comparison of recently published performance data for microfluidic artificial lungs. Data is from other reported works, or estimated from reported values. H is artificial capillary height. $\delta_M$ is membrane thickness. SAV is the surface-area-to-blood-volume ratio in the effective gas exchange area. SAGE is the percent of blood contacting surface area that contributes to gas exchange. Values in the table represent the maximum values for gas exchange. Values are calculated for the membrane area that is effectively contributing to gas exchange. Numbers in parenthesis include both the gas exchange and blood distribution regions to give total device values, when applicable.

| Source | H (μm) | $\delta_M$ (μm) | SAV (cm$^{-1}$) | SAGE % | O$_2$ Exchange mL O$_2$ · min$^{-1}$ · m$^2$ | CO$_2$ Exchange mL CO$_2$ · min$^{-1}$ · m$^2$ | Blood Flow mL · min$^{-1}$ · m$^2$ | Sweep Gas |
|---|---|---|---|---|---|---|---|---|
| Kniazeva 2012 | 50 | 30 | 200 | 36 | 358 | — | 11.7 | O$_2$ |
| Wu 2013 | 80 | 15 | 125 | 44 | 12 | 108 | 2.6 | Air |
| Rochow 2014 | 80 | 20 | 125 | 44 | 104 | 101 | 2.6 | O$_2$ |
| | 80 | 20 | 125 | 44 | 31 | 140 | 2.6 | Air |
| Kovach 2015 | 10 | 15 | 800 (109) | 34(4) | 133 (15) | 478 (54) | 6.3 | Air |
| Maquet Quadrox-i Small Adult | — | — | 74 | — | 227 | 246 | 3.8 | O$_2$ |

Table 4 provides a comparison of the sizing for scaled-up rolled and planar microfluidic artificial lung devices (102 mL O$_2$/min gas exchange). Calculations for planar devices were performed using data from Kniazeva et al. (2012) and Rieper et al. (2015) and for a planar version of the rolled device disclosed herein. The scaled-up forms of the Kniazeva and Rieper devices would require 3923 and 1133 gas exchange units, respectively, to reach 102 mL Oz exchanged per min. Based on the calculations in Table 4, it is apparent that the rolled device provides a smaller total device size compared to the planar devices for a fixed gas exchange. It is worth noting that the blood flow network and membrane sizes are different in each device, which can affect gas exchange efficiency and thus device size. A theoretical planar device using the disclosed blood flow network and assuming a fabrication method similar to that used in Kniazeva et al (2012) is also included in the table. Assuming gas exchange unit thicknesses similar to the Kniazeva device, the scaled up planar device would still be roughly twice as large as the rolled configuration.

In microfluidic artificial lungs, the drawback of this approach is the complexity of the blood flow network which contains multiple channel depths and must be carefully designed to achieve desired pressure drops and shear stresses.

Smaller capillaries can also be more susceptible to failure due to clotting due to their size and high surface area to volume ratio. Thus, true surface biocompatibility can be realized to reduce the risk of clotting within the device. Nevertheless, an inherent tradeoff exists between gas exchange efficiency and biocompatibility that can also be optimized.

While the rolled fabrication approach has many advantages, there are potential challenges to consider. First, challenges can be encountered due to the fact that the device is formed from a single mold. As the device is scaled up, this mold may become too long to be handled using the tools. The methods can be modified and increased in scale to permit the creation of rolled microfluidic artificial lungs with clinically relevant rated blood flows. Second, as devices are

TABLE 4

Theoretical device sizing for scaled-up microfluidic artificial lungs. Published gas exchange and sizing data was used to scale up to a basis of 102 mL O$_2$ exchange per min. Device dimensions are given as "diameter × length" for the rolled device, and "length × width × height" for planar devices. "N/A" signifies data was not available for the calculation.

| Device design | Theoretical Device Size (cm$^3$) | Gas Exchange Surface Area (m$^2$) | Device Dimensions (cm) | 2D Diffusion | Membrane Thickness (μm) | Blood channel depth (μm) |
|---|---|---|---|---|---|---|
| Rolled Device | 2411 | 0.66 | 15.2 × 14.2 | Yes* | 66 & 100 | 12 |
| Planar: Kniazeva 2012 | 4175 | N/A | 2.3 × 2.3 × 789 | No | 30 | 100 |
| Planar: Rieper 2015 | 9792 | 12.7 | 16 × 10 × 61.2 | Yes | 90 & 90 | 200 |
| Planar: (Current design) | 5079 | 0.66 | 1.1 × 15.2 × 300 | No | 66 | 12 |

*Calculated values do not take into account improvements in performance due to two-directional gas exchange in the rolled device and thus represent worst case values.

As devices are scaled to larger flow rates for clinical application, artificial capillary depth can be an important design consideration. Smaller capillaries provide more efficient gas exchange, but present important challenges as well, particularly related to pressure drop and clotting. With all other variables held constant, as vessel diameter decreases, pressure drop will increase. However, a solution is to decrease vessel length so that the pressure drop stays low, resulting in a large array of small diameter vessels in parallel. This strategy is evident in the natural lung as well.

scaled up and the number of stacked layers is increased, fluidically interconnecting the layers while maintaining physiological shear stress can become more challenging. Currently, a scalpel or biopsy punch is used to make fixed-diameter fluidic connection between multiple layers. As the number of layers and device thickness increases, having a fixed diameter feedthrough may result in varying shear stress throughout the feedthrough thereby potentially resulting in blood stagnation and clotting. By adjusting the diameter and cutting angle of these feedthroughs, it is possible to create feedthrough which has a diameter that decreases in size with decreasing depth. Such an approach may produce relatively constant and approximately physiologic shear stress throughout the feedthroughs. Finally, unwanted adhesion between the PDMS and substrate can cause ripping of the PDMS sheet. This is not uncommon to the rolled fabrication method, but is a concern for designs which incorporate thin PDMS sheets which are susceptible to tearing. A thicker sheet can be more resistant to tearing, but may produce a device with thicker gas exchange membranes—presenting a potential tradeoff between device performance and repeatability. The risk of tearing can be minimized, however, by minimizing the adhesion between the PDMS and the patterned substrate.

Example 3: Microfluidic Artificial Lungs

The systems and methods disclosed herein were implemented to improve rehabilitation from lung disease by engineering a portable artificial lung capable of acute and chronic pulmonary support. Microfluidic artificial lungs (μALs) promise to enable a new class of truly ambulatory artificial lungs through feature sizes and blood flow networks that closely mimic those in their natural counterpart. These new artificial lungs can: 1) have surface areas and priming volumes that are a fraction of current technologies thereby decreasing device size and reducing the foreign body response; 2) contain blood flow networks in which cells and platelets experience pressures, shear stresses, and branching angles that copy those in the human lung thereby improving biocompatibility; 3) operate efficiently with room air, eliminating the need for gas cylinders and complications associated with hyperoxemia; 4) exhibit biomimetic hydraulic resistances, enabling operation with natural pressures and eliminating the need for blood pumps; and, 5) provide increased gas exchange capacity enabling respiratory support for active patients. Disclosed herein are: the highest efficiency artificial lung to date, enabling air to be used effectively as the sweep gas; a theoretical model that accurately predicts gas exchange in μALs; application of hydrophilic coatings to the blood contacting surfaces in μALs that significantly increased biocompatibility and device lifetime; a comprehensive design optimization procedure for μALs; a μAL with the highest rated flow to date, thereby significantly decreasing the number of layers required to construct a human-scale device; methods that demonstrated that nitric oxide in the sweep gas extended the lifetime of devices in vitro; and, a manufacturing technique similar to roll-to-roll manufacturing capable, with modifications, of creating human-scale artificial lungs. Also disclosed is a human-scale μAL that was constructed and tested as described below. Disclosed herein are small-scale, single layer microfluidic artificial lungs with excellent gas exchange efficiency, allowing air to be used effectively as the sweep gas. Using air as the sweep gas increases portability (by eliminating gas cylinders) and decreases the complications associated with hyperoxemia (including increased mortality and up-regulated platelet activation/aggregation). Through the precise control afforded by microfabrication, blood flow networks have been implemented that closely mimic the natural vasculature in terms of vessel diameters, branching angles, pressure, and shear rate, thereby providing a natural environment for blood cells. To improve biocompatibility, hydrophilic surface coatings have been used to reduce protein and platelet deposition and increase device lifetime. Endothelial cells can be confluently grown on the surfaces of microfluidic blood flow networks and can decrease thrombus area. Despite the promise of these single layer microfluidic artificial lungs, their rated blood flows were a small fraction of what is needed for human applications. Thus, manufacturing methods of scaling up to increase the blood flow capacity of microfluidic artificial lungs and move these devices towards clinical application are required. Two such techniques have been demonstrated to date. In the first, microfluidic artificial lungs consisting of flat, two-dimensional blood flow manifolds are stacked vertically and connected via common blood and gas flow inputs and outputs. This method requires many manual steps and automation is problematic. In the second and exemplary method, as shown in FIGS. 6B-C, a polymer sheet comprising both blood and gas flow channels can be wrapped around a cylindrical substrate in a manner similar to roll-to-roll polymer sheet processing.

Figure 12:
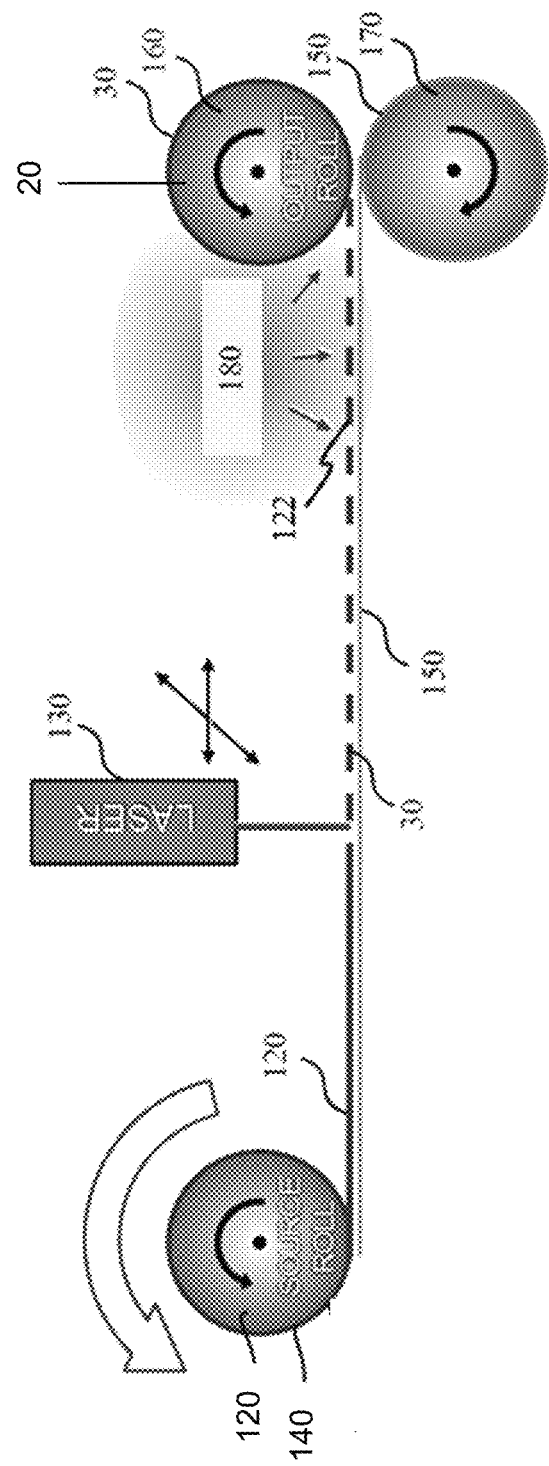
FIG. 12 shows a diagram of an exemplary roll-to-roll manufacturing system, as disclosed herein.

Roll-to-roll (R2R) processing is an industrial and research manufacturing process used to create large areas of flexible electronic devices (e.g. solar cells, displays, smart sensors, thin film batteries) on a flexible substrate. A typical R2R process starts with a roll of a thin polymeric film termed a "film" or "web". The film can be unrolled from a source spool, processed using additive and/or subtractive manufacturing to add features and/or electronics, and then re-rolled onto an output spool. A custom R2R system is used to manufacture the human-scale microfluidic artificial lungs disclosed herein (FIG. 12).

Overall, the disclosed R2R-based artificial lung technology can provide improved rehabilitation of patients suffering from respiratory disabilities through three means: 1) improved gas exchange compared to current devices to permit complete, ambulatory respiratory support of active patients; 2) increased biocompatibility to increase device lifetime, permit long-term treatment, and increase patient health; and 3) increased portability to permit ambulatory care and improved patient quality of life. Following integration into various complete systems, the disclosed device can provide lung rest for patients suffering from pulmonary disabilities, serve as a bridge to transplant for patients with chronic lung disease and lung cancer, and lead to the development of the first implantable artificial lung for semi-permanent support. In addition, the device can be applied in portable heart-lung machines for first responders and combat medics.

Disclosed is a wearable arteriovenous (AV) extracorporeal $CO_2$ removal (ECOOR) system for end stage lung disease (ESLD). ECOOR can promptly relieve the symptoms of ESLD, improve oxygenation and decrease pulmonary hypertension, and allow rehabilitation. The amount of blood flow required to remove the metabolically produced $CO_2$ is about 20% of the total cardiac output. $CO_2$ removal between >200 mL/min has been achieved by using large sweep gas flow rates (4-16 L/min) in artificial lungs with rated flows of as low as 1.5 L/min. Moreover, $CO_2$ removal is the same in arterial or venous blood and thus an artificial lung for $CO_2$ removal can be driven by arterial pressure, eliminating the need for a blood pump. Thus, a wearable AV ECOOR system can provide effective palliation to many ELSD patients and can allow ambulation and rehabilitation.

Also disclosed herein is a wearable AV ECOOR system as a small enclosure strapped to the hip or chest that contains an artificial lung, a battery pack, a light weight air pump, and a simple control system to allow for charging of the battery pack and adjustment of the air pump. Blood flow can be driven by the heart and vascular access can be achieved using vessels that permit ambulation (i.e. subclavian artery and vein).

Specifications for such an AL are: 1) blood flow of ~20% of cardiac output (1 L/min at rest); 2) $CO_2$ clearance of 100-250 mL/min (half or more of the metabolically produced $CO_2$ at rest and exercise); 3) small blood-side resistance to permit adequate blood flow with AV pressures; and 4) gas sweep flow at 1-16 L/min for adequate $CO_2$ removal. Such a system can primarily remove $CO_2$, but can also deliver some $O_2$ at 1 L/min blood flow (10-20 mL/min if $SO_2$ increases from 90 to 100%). This is similar to the oxygen delivery that is delivered to the patient when inhaled $O_2$ is supplemented with an oxygen generator. In addition to $CO_2$ retention, some patients with ESLD also have profound hypoxemia that is exacerbated during exercise. While these patients may not benefit from the initial system disclosed herein, they can be treated with a venovenous (VV) configuration, as disclosed herein. Briefly, a dual lumen venous catheter can be inserted into the jugular vein, and a small pump (e.g. the Abiomed Impella) can be added to the system to drive blood flow through the device. The methods and systems described herein can result in a microfluidic artificial lung with a rated blood flow of 1 L/min that has been validated in acute and chronic animal studies.

Also disclosed herein are: a) the first manufacturing process capable of creating large area microfluidic devices; and, b) the first human-scale microfluidic artificial lung.

Figure 6D:
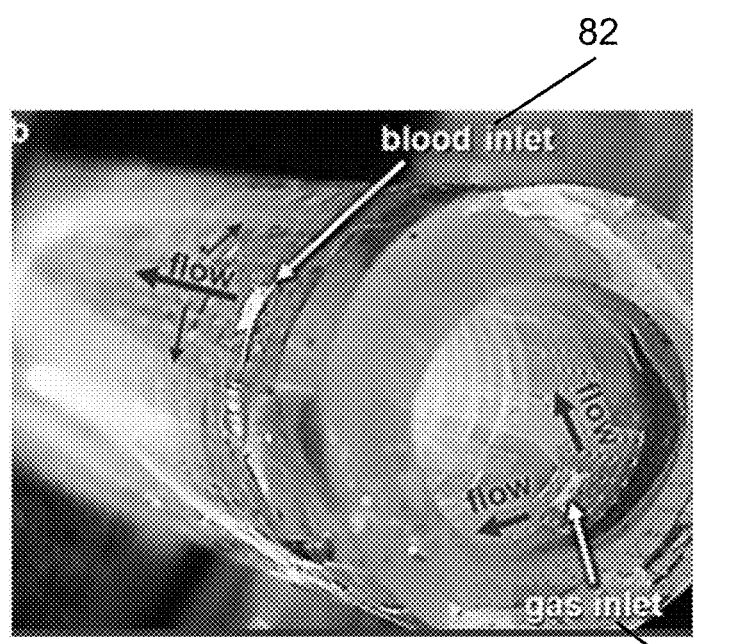

Rolled-Membrane Construction Process: Disclosed herein is a rolled-membrane construction process for microfluidic artificial lungs and its demonstrated effectiveness in small scale devices through testing with bovine whole blood. This rolled-membrane process was described fully in Example 2 and can be extended and modified to create the first human-scale microfluidic artificial lungs using the disclosed R2R manufacturing process for microfluidic artificial lungs. In the rolled-membrane process, the layers were contained in a single polydimethyl siloxane (PDMS; a gas permeable biomaterial) sheet and the multi-layer device was formed when this sheet was rolled onto and bonded to a cylindrical substrate. Each revolution of the rolling process formed a new, overlapping layer, resulting in many closely packed blood, membrane, and air layers. The creation of a two-layer (one blood, one air) device using this process is shown in FIGS. 6A-D. First, PDMS was spun onto a silicon wafer containing a photoresist mold with features for the air and blood layers. More particularly, the features corresponded to a plurality of liquid flow channels within a liquid (e.g., blood) flow layer and a plurality of gas flow channels within a gas flow layer. The layers were formed sequentially along the length of the PDMS membrane, and each layer was designed to cover one complete circumference of the cylindrical substrate (PDMS tubing in FIG. 6A) as the PDMS tubing is rolled along the length of the molded PDMS membrane. Prior to rolling, the contacting edges of the tubing and the molded PDMS sheet were then exposed to oxygen plasma and brought into contact to form an initial irreversible bond (FIG. 6A). Additional plasma treatments were then performed followed by rolling the tubing along the length of the PDMS sheet until completion (FIG. 6D). Fluidic feed-throughs were cut through the multi-layer device using a scalpel (FIG. 6D) and fluidic tubing was attached using silicone epoxy (FIG. 6B). FIG. 6C shows a cross-section of the rolled membrane and displays the multi-layer structure. Expected blood side pressure drop and gas exchange were verified using bovine blood. It is contemplated that the rolled-membrane process described herein (and in detail in Example 2) can be expanded to a true roll-to-roll process capable of producing human-scale microfluidic artificial lungs.

Laser Engraved Flow Channels in PDMS: Laser engraving flow channels in PDMS were studied. Laser (Epilog Zing 24 30W) power was varied between 1 and 15% resulting in channels with depths between 30 and 200 μm and widths between 80 and 250 μm (FIG. 11). Channel cross-sectional shape varied from ovular (low power) to rounded triangular (higher power). After rinsing with acetone, laser engraved PDMS films were successfully bonded together using a standard plasma oxidation process. Laser engraving can be used to form flow channels in the human-scale microfluidic artificial lungs disclosed herein.

Design of Human-Scale R2R Microfluidic Artificial Lungs: Disclosed herein is a design for the humans-scale microfluidic artificial lungs developed using the optimization procedure described herein (FIGS. 11A-D). The design can feature a cylindrical topology (FIG. 11B) and be formed by rolling up a laser engraved PDMS sheet. Sweep gas flow can occur from the top to the bottom and radially inside of the device. Blood can flow into the side of and through the artificial capillaries in the cylinder. An injection molded polyurethane enclosure (light gray, FIGS. 11A-11D) can route blood to/from the artificial capillaries. $O_2$ and $CO_2$ diffusion can occur through both the top and bottom of the artificial capillaries (FIG. 12D).

Figure 11E:
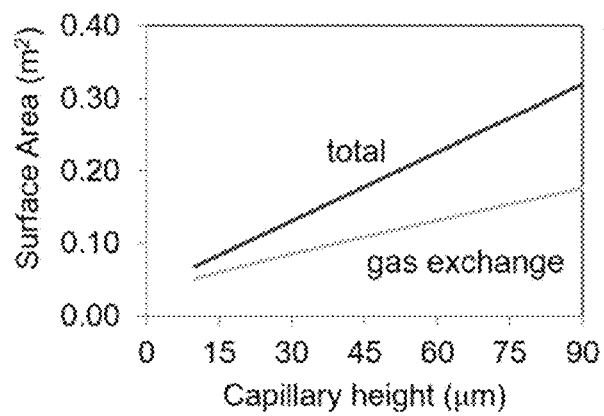
Figure 11F:
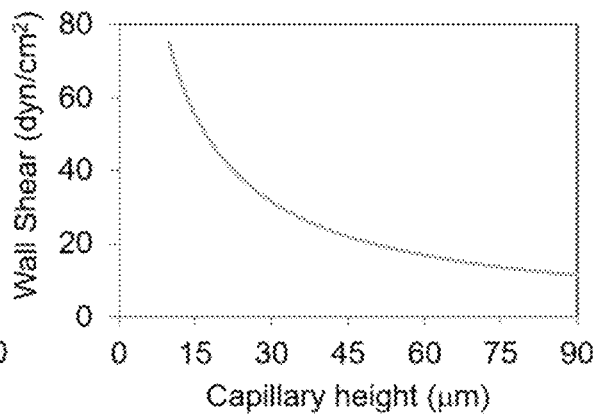
Figure 11G:
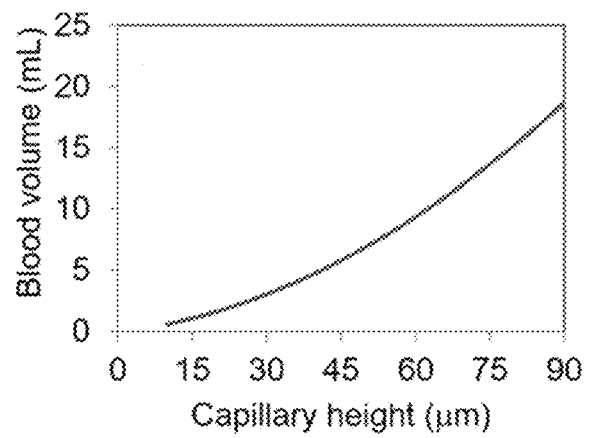

Analytical equations were used to model various performance metrics for this design (FIGS. 11E-F). Rated blood flow (the blood flow at which blood entering the artificial lung with an oxygen saturation of 70% exits the device at 95%) of the device was fixed at 1 L/min and the pressure drop of the artificial capillaries was fixed at 50 mmHg (to be compatible with pumpless operation via peripheral AV attachment; see specifications above). PDMS layer/film thickness was fixed at 100 μm. Sweep gas was $O_2$. Gas and liquid flow channels were assumed to be laser engraved in the PDMS film. Gas channel height was fixed at 70 μm and artificial capillary height was varied between 10 and 90 μm. Results are shown in FIGS. 11E-H.

Figure 11H:
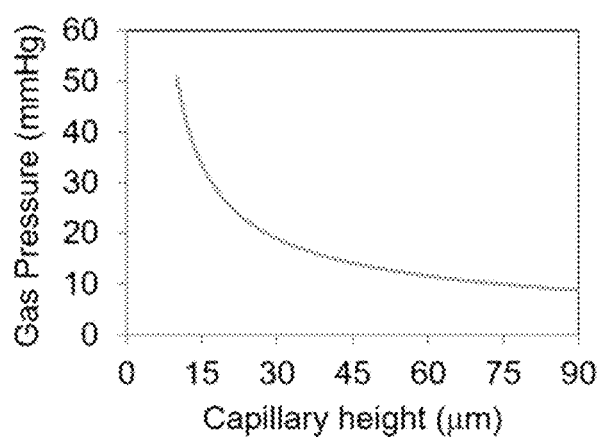

For any blood contacting device, it is desirable to minimize the blood contacting surface area and the blood volume ("priming volume"). Minimizing surface area can minimize the body's immune response and reducing priming volume of artificial lung circuits during cardiopulmonary bypass procedures can improve outcomes. To avoid pressure driven gas flow across the membrane (and thus gas emboli in blood), the maximum gas side pressure in an artificial lung should not exceed its minimum blood side pressure. For a pumpless configuration, the minimum blood side pressure is approximately venous pressure plus the tubing pressure drop or ~20 mmHg. Capillary heights greater than 25 μm result in a gas side pressure drop less than 20 mmHg (FIG. 11H). In order to minimize platelet activation and cell lysis, shear stress in an artificial lung should be similar to that seen in the natural vasculature. In the human vascular system, shear stress ranges between 10 and 70 $dyn/cm^2$ in arteries and between 1 and 6 $dyn/cm^2$ in veins. Further, the human body naturally compensates to maintain a mean arterial shear stress between 15 and 20 $dyn/cm^2$. All capillary heights (FIG. 11F) greater than 12 μm provide a shear stress in the physiologic range.

Finally, the disclosed design can be compatible with the capabilities of the manufacturing system. Tests with the laser system (Epilog Zing 24) indicate that it is feasible to reliably produce artificial capillaries with heights greater than 40 μm. Thus, to minimize blood contacting surface area, artificial capillary height is set to 40 μm, resulting in upper and lower membrane thicknesses of 60 and 30 μm (because film thickness is fixed at 100 μm). The total blood contacting surface area is 0.16 m², total blood volume is 4.8 mL, and gas side pressure is 15.4 mmHg. For a starting inner diameter of 5 cm, the disclosed device can have an outer diameter of 6.6 cm and width of 7 mm. The microfluidic artificial lung can have 74 layers and be built from a 12.3 m-long PDMS film. The microfluidic artificial lung can exchange ~40 mL/min of $O_2$ using oxygen as the sweep gas or ~15 mL/min of $O_2$ using air as the sweep gas. The polyurethane enclosure can add an additional ~0.03 m² to the blood contacting surface area and ~8 mL to the priming volume (0.19 m² and 13 mL total). For comparison, if the state-of-the-art Novalung iLA Membrane Ventilator were scaled down to a rated flow of 1 L/min, it would have a blood contacting surface area of 0.31 m² and a total blood volume of 39 mL.

Manufacturing Techniques to Create Human-Scale Microfluidic Artificial Lungs

The rolled-membrane process described above was modified and extended resulting in the disclosed custom roll-to-roll (R2R) system capable of creating the first human-scale microfluidic artificial lung (and the first large area microfluidic device).

No techniques currently exist to create large area microfluidic devices or human-scale microfluidic artificial lungs. A method of stacking multiple microfluidic artificial lung in parallel has been investigated, but hundreds to thousands of the devices would be required to achieve rated blood flows suitable for adults. Disclosed above (Example 2) is a manual "rolled-membrane" manufacturing method that creates a cylindrical microfluidic lung. In this method, a PDMS film can be first patterned using a mold, then surface activated, and rolled onto a cylindrical substrate to form the final device. The main drawbacks of this approach were its manual nature and the need for a physical mold. For a human-scale device, such a mold would need to be many meters long, making this approach impractical. To overcome these drawbacks, the disclosed automated R2R manufacturing method was developed. To eliminate the need for a mold, the system can use a preformed roll of medical grade silicone sheeting (a thin 100 um PDMS film) manufactured by, for example, Vesta Inc. of Franklin, Wis. and the blood and liquid flow channels can be engraved in the surface of the silicone sheeting, e.g. using a $CO_2$ laser.

Methods: A diagram of the disclosed R2R system is shown in FIG. 12. A pre-formed roll 140 of medical grade silicone (Vesta, Inc.; 6" wide) was unrolled, laser engraved to form the various gas and liquid flow channels and diffusion membrane, plasma treated to activate the surface and enable layer-to-layer bonding, and then rolled up onto a cylindrical surface 20 to bond each layer to the next and form the device. The cylindrical surface 20 was positioned on an output roller 160. After construction, the artificial lung was sealed in a custom polyurethane enclosure to form gas and blood flow connections. There are considerations that should be accounted for in the design of the R2R system related to the assembly of the microfluidic artificial lung. First, to successfully bond, each silicone layer needs to be plasma activated for 30 seconds and then immediately brought into contact with the adjoining layer. Second, to perform accurate laser engraving, the web should be stationary and a fixed distance from the laser. To account for these concerns, the rolling process can occur in a step-wise manner. That is, a 5 cm length of the web can be unrolled, stopped, and held stationary for 30 seconds. While stationary, a plenum under the laser can pull a slight vacuum on the web to hold it stationary and provide a repeatable, fixed distance from the laser to the film. The laser 130 can then be activated to create flow channels in that 5 cm of the web. Also while stationary, the silicone web near the output rolls 160, 170 is being exposed to a plasma treatment 180, which activates the surface for subsequent bonding. After the 30 second period is over, the plenum vacuum can be released and the film can be advanced. When the film is advanced, the portion of the web that was just surface activated can be rolled onto the output roll 160, bringing it in intimate contact with and bonding it to the silicone layer already on the output roll. Given an expected plasma exposure width of approximately 5 cm, the resulting average linear velocity of the web is about 1.6 mm/s. For the design of a human-scale microfluidic artificial lung, the total required silicone web/film length is approximately 12.3 m, resulting in a total manufacturing time of approximately 2 hours. Each silicone roll can fit approximately 20 human-scale microfluidic artificial lung in its 6" width, resulting in an average manufacturing time of 6 min per device.

Next, alignment of the various components is important to achieving a working final device. Side to side (left to right) and rotation tracking is important when feeding the silicone sheet into the laser area and onto the output spool. The R2R system can incorporate a system to manually monitor (magnified edge on roller) and adjust skew/taper of the sheeting as it feeds into the laser area. If a left/right deviation greater than 1 mm is detected, the rolling process can be temporarily stopped and the alignment adjusted using a manual and precise skew/taper control. This system can be automated. Skew and rotation of the output roll relative to webbing/sheeting is also important to avoid misalignment and wrinkling of the rolled film and can be monitored and adjusted (if necessary) using the same process described herein.

Optimize Performance of the Microfluidic Artificial Lung for its Clinical Application.

Disclosed are methods for optimizing the surface area, pressure drop, priming volume, size, and shear stress of the disclosed human-scale microfluidic artificial lung for its clinical application, AV ECOOR for ESLD.

Methods: An initial design for the human-scale microfluidic artificial lung was developed using the disclosed optimization procedure. That initial design can comprise a simple array of straight liquid flow channels of a single height. That same procedure can be applied to a greater number of design variations (using a branching blood flow network with two channel heights; flip the orientation of gas and blood flow; etc.). The top performing design (smallest surface area and priming volume for a fixed rated flow and pressure drop) can be simulated using computational fluid dynamics (CFD) to minimize flow anomalies and stagnation and provide a uniform and physiological shear stress throughout the blood flow network. Completed microfluidic artificial lung was built using the R2R system disclosed herein, housed and sealed (using medical grade silicone) in a custom polyurethane enclosure (FIG. 11A), modified with the disclosed protein-resistant hydrophilic coating, and then tested in vitro with anticoagulated whole bovine blood to measure gas exchange and pressure drop (vs. blood flow) and to visualize residual clots after flushing with PBS.

Data Analysis: At least three devices were tested in the in vitro experiments to verify repeatability. Measurements were converted to means and standard deviations and compared to theoretical values at each blood flow using Tukey's test. Results were deemed significant for $p<0.05$. The optimized device can have a rated flow greater than 1 L/min and pressure drop less than 70 mmHg.

Results: A microfluidic artificial lung with a rated blood flow of 1 L/min and pressure drop suitable for AV operation (<70 mmHg @ 1 L/min) was developed.

The custom polyurethane housing may leak and can be redesigned to improve sealing, if required. PDMS contact angle may degrade between surface activation and coating due to the extended manufacturing time. If so, other techniques (e.g., exposure to ozone or acid solution) can be used to modify the PDMS after microfluidic artificial lung construction. If an issue occurs with the R2R system, a microfluidic artificial lung consisting of ~50 of the disclosed planar device stacked in parallel (rated blood flow ~1 L/min) can be used.

Validate Performance and Biocompatibility in Acute and Chronic Sheep Models

The disclosed human-scale microfluidic artificial lung was evaluated in both acute and chronic sheep models that mimic the clinical application: arteriovenous carbon dioxide removal for ESLD.

In vitro studies can quantify gas exchange and pressure drop and provide initial indications of biocompatibility. However, in vitro studies are not adequate to provide the information necessary to determine acute and chronic biocompatibility, the systemic adverse effects of the devices, and whether the microfluidic artificial lung can be effective in preventing symptoms of ESLD. Because of the need for whole animal physiology, animals were used to test the capabilities of the disclosed human-scale artificial lung. Acute and chronic ovine models of arteriovenous (AV) carbon dioxide removal were used to specifically test AV carbon dioxide removal by an artificial lung (i.e., gas exchange and biocompatibility of the human-scale µAL). In the acute model (in anesthetized sheep), precise control of animal PaCO2 was achieved through control of minute ventilation (MV), thereby permitting the symptoms of ESLD to be mimicked in sheep (and alleviated through microfluidic artificial lung intervention). The chronic model (in awake healthy sheep) allowed long term testing of device biocompatibility as well as the impact of microfluidic artificial lung $CO_2$ removal on animal physiology (via changes in animal respiratory rate).

Acute 8 h Sheep Study for the Microfluidic Artificial Lung (Non-Recovery)

An acute in vivo study was conducted to validate microfluidic artificial lung function, biocompatibility, and its impact on physiology in a large animal model. In vitro tests simply will not provide the necessary information. The knowledge gained will allow us to implement design changes, if necessary, before chronic animal studies.

Methods: Animals were anesthetized and paralyzed, then surgically prepared for subclavian AV extracorporeal $CO_2$ removal. For anticoagulation, a heparin infusion was titrated to maintain an activated clotting time (ACT) between 200-250 seconds. After all preparations were complete, the microfluidic artificial lung was attached in the AV circuit, initially with no sweep flow. Hypercarbia was induced in the animal by decreasing minute ventilation from 100% baseline to 75% and 50% (80 mL/kg/min, 60 mL/kg/min, and 40 mL/kg/min, respectively). The animal's arterial $CO_2$ content ($PaCO_2$) was allowed to stabilize. 50% MV resulted in an animal $PaCO_2$ 74±7 mmHg which is clinically relevant for ESLD. Gas exchange and $PaCO_2$ was then measured for blood flows of 0.5, 0.75, and 1.0 L/min and blood to sweep flow (air) ratios of 1:1, 1:2, 1:4, and 1:8 at 0, 15, and 30 min after initiation of sweep gas. Animal $PaCO_2$ stabilized in 20 minutes under similar conditions. After the measurements for a specified blood and sweep flow were complete, sweep flow was turned off and animal $PaCO_2$ was allowed to return to baseline before the next test was initiated. These acute experiments can last up to 8 hrs. The entire preparation was repeated in 5 sheep to evaluate reproducibility of the results and obtain statistical significance. The schedule of measurements is provided in Table 5 below.

TABLE 5

Physiologic and device measurement during acute and chronic animal experiments

| VARIABLE | MEASUREMENT/DESCRIPTION | FREQ |
|---|---|---|
| Systemic Hemodynamics | Arterial line: heart rate (HR), blood pressure (mean arterial pressure, systolic and diastolic); Pulmonary artery (PA) line: central venous pressure, mixed-venous $O_2$Sat; pulmonary artery pressure, core body temperature. Cardiac output (CO): Thermodilution | Acute and Chronic: At baseline, then monitored continuously (reported hourly) |
| Blood Chemistry | Blood chemistry and metabolic panel: Renal function (BUN, Creatinine); Hepatic enzymes (AST, ALT), electrolytes, amilase and lipase using IDEXX Catalyst Dx cheestryl analyzer (17-panel clip). | Acute: Pre-operative Chronic: At Day 1, 4, 7, 10, and 14 |
| Pulmonary | Respiratory rate (RR); Arterial and post AL blood gases and saturation during settings described in protocol, above: Hemoglobin, Hematocrit, $PO_2$, $PCO_2$, pH, Hb, metHb, $HCO_3$ with a Radiometer ABL 725; Copenhagen, Denmark. | Acute: At baseline, then at each data point. Chronic: At baseline, then twice daily |
| Hematology and Coagulation | ACT with Hemochron Blood Coagulation System; International Technidyne Corp., Edison, NJ | Acute: At baseline, then every hr Chronic: At baseline, then every 4 hrs |
| | Complete Blood Count with differential, blood chemistry using IDEXX ProCyteDx hematology analyzers. | Acute: At baseline Chronic: At Day 1, 4, 7, 10, and 14 |
| | Platelet count, activation and function via flow cytometry (glycoprotein P-selectin expression); Platelet aggregometry; Fibrinogen; D-dimers TEG using the TEG500 Hemostasis analyzer system (Braintree, MA); Blood coagulation times via a Dade Behring BCS coagulation analyzer. | Acute: N/A Chronic: At Day 1, 4, 7, 10, and 14 |

TABLE 5-continued

Physiologic and device measurement during acute and chronic animal experiments

| VARIABLE | MEASUREMENT/DESCRIPTION | FREQ |
| --- | --- | --- |
| Tissue | Histology (H&E): Lung- assessment for embolism, edema, hemorrhage, neutrophil infiltration, microvascular thrombosis; Blood/skin site cultures. | Acute: N/A Chronic: End of the study |
| Microfluidic Artificial Lung | Blood flow, device pressures, calculated resistance | Monitored continuously (Acute: reported at each data point; Chronic: reported hourly) |
|  | CO2 removal rate vs. sweep flow; Impact on respiratory rate | Acute: Hourly; Chronic: once daily |
|  | ACTs, inspection for clots, time to occlusion (clotting) | Acute: Hourly; Chronic: Every 4 hrs |
|  | Artificial lung removed, flushed, and examined for clots | Acute and Chronic: End of the study |

Data Analysis: The primary endpoints are animal $PaCO_2$ and microfluidic artificial lung function ($CO_2$ exchange and thrombosis). For each 15-minute increment, arterial $CO_2$ and artificial lung settings (blood flow/sweep flow) can be recorded for each minute ventilation scenario (100%, 75%, and 50%) to maintain gas exchange and hemodynamic stability during the duration of the study. Animal $PaCO_2$ and gas exchange at each data point for all five animals was combined into means and standard deviations. Baseline $PaCO_2$ were compared to $PaCO_2$ after the animal stabilizes during microfluidic artificial lung support using Tukey's test. Results were deemed significant for $p<0.05$.

Results: The application of the microfluidic artificial lung successfully reduces animal $PaCO_2$ and reduction increases with increasing blood flow and sweep flow. The microfluidic artificial lung is able to remove all metabolically produced $CO_2$ for optimal blood and sweep flow settings. That is, for 50% MV (staring animal $PaCO_2$ of 60-80 mmHg), application of the microfluidic artificial lung achieves a systemic $PaCO_2$ of 30-40 mmHg (normal for sheep) within 10 to 20 minutes.

Chronic 14 d Sheep Study for the Microfluidic Artificial Lung (Recovery)

The methods disclosed herein were conducted to: 1) evaluate microfluidic artificial lung lifetime and biocompatibility; 2) monitor $CO_2$ removal over time; and, 3) determine impact of the microfluidic artificial lung on animal physiology (via a reduction in respiratory rate) during 14 day AV ECOOR support in the ICU in 10 animals. One group (n=5) received an unmodified microfluidic artificial lung and standard sweep gas and the second (n=5) received a coated microfluidic artificial lung (hydrophilic sulfobetaine) with 1000 ppm NO in the sweep gas (plus any additional anti-thrombotic strategies described herein.

Feasibility and efficacy of the device were demonstrated during acute studies and continued in this chronic study. In vitro and acute in vivo studies cannot be used to measure device lifetime or long-term effects on animal physiology. Two experimental groups (unmodified microfluidic artificial lung vs. coated microfluidic artificial lung with NO in sweep gas) can permit measurement of the disclosed anti-thrombotic strategies and their impact on device lifetime and animal physiology.

Methods: In normal sheep, subclavian AV access was established as described herein. Cannula was secured and tunneled subcutaneously to exit the animal's upper back. Following surgery, sheep were recovered, extubated, and transferred to the sheep ICU (ShICU) for extended monitoring. In the ShICU, the sheep were maintained in a customized restraining cage under 24 h surveillance by staff. After recovery and stabilization, the microfluidic artificial lung was primed with crystalloid and attached to the AV shunt. Heparin was titrated to animals with a target ACT of 200-250 s. Sweep gas was 5% $CO_2$ and 95% air so the microfluidic artificial lung has no effect on gas exchange and animal physiology, except when gas exchange and respiratory rate are measured as described herein. This chronic animal protocol included continuous and daily data collection (Table 5). Microfluidic artificial lung thrombosis was estimated by measuring the device resistance continuously. Twice daily, the ability of the microfluidic artificial lung to alleviate the symptoms of ESLD was measured by temporarily switching to 100% air sweep gas flow and measuring $CO_2$ removal rate, $PaCO_2$, and respiratory rate. Measured $CO_2$ exchange can also serve as a secondary measure of clotting. If the device resistance is twice baseline the device can be replaced.

Data Analysis: Time to device failure and number of device exchanges over 14 days were the primary end points. Surrogate measures of device thrombus over time were secondary end points (device resistance & gas exchange). The many other secondary end points (hemodynamics, hematology, physiology, blood chemistry) were used as safety data. Means, standard deviations, maximums, and minimums were estimated and summarized for lab values (taken at days 1, 4, and 7), hemodynamic and physiologic data. Qualitative data including coagulation, AL clotting, and histologic evaluation were evaluated. Critical care and mechanical problems were documented descriptively. Gas exchange rates were calculated from blood gas measurements. Blood-side fluidic resistance was calculated from pressure and flow data. Baseline (5% $CO_2$ sweep gas) $PaCO_2$ and respiratory rate were compared to the same values during ECOOR support (100% air sweep gas) using Tukey's test. Results were deemed significant for $p<0.05$.

Results: The microfluidic artificial lung in heparinized sheep functions without clotting for 14 days and hemodynamic data was within normal range in all animals. The microfluidic artificial lung can operate for at least 3 days before an exchange is required, permitting initial acute clinical applications in the ICU setting to treat $CO_2$ retention due to exacerbations of ESLD.

There is a chance that the microfluidic artificial lung may malfunction due to clotting, water in the gas phase, or insufficient $CO_2$ clearance. Water in the gas phase can be cleared using a momentary high sweep flow. If the artificial lung clots, it can be replaced. Other potential problems are inherent to chronic sheep experiments: anemia from blood sampling and bleeding, line clotting or malfunction, mechanical damage caused by sheep activity, failure of measurement apparatus. It is unlikely but possible that metHb will increase or MAP will decrease due to NO in the sweep gas. If this occurs, NO flow can either be decreased or stopped and the tests resumed. If any issue arises with the R2R manufacturing system, it is possible to use a microfluidic artificial lung consisting of ~50 of the disclosed planar devices stacked in parallel, resulting in a rated blood flow of 1 L/min.

As described in detail herein, microfluidic artificial lungs can be applied to advance rehabilitation from lung disease. The disclosed automated roll-to-roll manufacturing method can be employed, which, for the first time, is capable of quickly and easily constructing large area microfluidic devices. The disclosed systems and methods provide an understanding of the mechanisms underlying coagulation in microfluidic artificial lungs. As a result, the disclosed human-scale microfluidic lung was developed and its operation was proven in acute and chronic animal experiments, as described herein.

Exemplary Aspects

In view of the described products, systems, and methods and variations thereof, herein below are described certain more particularly described aspects of the invention. These particularly recited aspects should not however be interpreted to have any limiting effect on any different claims containing different or more general teachings described herein, or that the "particular" aspects are somehow limited in some way other than the inherent meanings of the language literally used therein.

Aspect 1. A microfluidic diffusion device comprising:
a cylindrical substrate having a central axis and an outer surface;
a patterned membrane rolled circumferentially over the outer surface of the cylindrical substrate to define a plurality of concentric membrane layers extending radially outwardly from the central axis of the cylindrical substrate,
wherein at least one membrane layer of the plurality of concentric membrane layers is patterned to define a plurality of gas flow channels that are configured to receive a gas,
wherein at least one membrane layer of the plurality of concentric membrane layers is patterned to define a plurality of liquid flow channels that are configured to receive a liquid, and
wherein the at least one membrane layer permits diffusion of:
(a) gas from the plurality of gas flow channels into the liquid within the plurality of liquid flow channels; or
(b) liquid from the plurality of liquid flow channels into the gas within the plurality of gas flow channels; or
(c) both (a) and (b).

Aspect 2. The microfluidic diffusion device of aspect 1, wherein the plurality of gas flow channels are configured to receive a gas, wherein the plurality of liquid flow channels are configured to receive blood, and wherein the at least one membrane layer permits diffusion of the sweep gas from the plurality of gas flow channels into the blood within the plurality of liquid flow channels.

Aspect 3. The microfluidic diffusion device of aspect 1 or aspect 2, wherein the patterned membrane comprises a single contiguous sheet of material.

Aspect 4. The microfluidic diffusion device of aspect 3, wherein the patterned membrane comprises a web or film of polydimethylsiloxane (PDMS).

Aspect 5. The microfluidic diffusion device of any one of the preceding aspects, wherein the patterned membrane has a maximum thickness ranging from about 10 μm to about 250 μm.

Aspect 6. The microfluidic diffusion device of aspect 5, wherein the plurality of gas flow channels are patterned to have a thickness ranging from about 10 μm to about 250 μm.

Aspect 7. The microfluidic diffusion device of aspect 5, wherein the plurality of liquid flow channels are patterned to have a thickness ranging from about 5 μm to about 250 μm.

Aspect 8. The microfluidic diffusion device of any one of aspects 3-7, wherein the plurality of gas flow channels and the plurality of liquid flow channels are engraved in respective portions of the patterned membrane.

Aspect 9. The microfluidic diffusion device of any one of the preceding aspects, wherein at least one membrane layer of the plurality of concentric membrane layers does not comprise gas or liquid flow channels.

Aspect 10. The microfluidic diffusion device of any one of aspects 3-9, wherein the plurality of concentric membrane layers comprise:
a liquid flow layer bonded to the outer surface of the cylindrical substrate and comprising the plurality of liquid flow channels;
a gas flow layer positioned radially outwardly of the intermediate layer and bonded to the liquid flow layer, wherein the gas flow layer comprises the plurality of gas flow channels; and
a capping layer positioned radially outwardly of the gas flow layer and bonded to the gas flow layer to cap the plurality of gas flow channels,
wherein the capping layer does not comprise gas or liquid flow channels, and wherein portions of the patterned membrane positioned circumferentially between the plurality of gas flow channels and the plurality of liquid flow channels permit diffusion of gas from the plurality of gas flow channels into the plurality of liquid flow channels.

Aspect 11. The microfluidic diffusion device of aspect 10, wherein plurality of gas flow channels and the plurality of liquid flow channels are oriented parallel or substantially parallel to the central axis.

Aspect 12. The microfluidic diffusion device of any one of aspects 3-9, wherein the plurality of concentric membrane layers comprises:
a plurality of gas flow layers, each gas flow layer comprising a portion of the plurality of gas flow channels; and
a plurality of liquid flow layers, each liquid flow layer comprising a portion of the plurality of liquid flow channels,
wherein the gas flow layers and the liquid flow layers are positioned in an alternating pattern moving radially outwardly from the central axis.

Aspect 13. The microfluidic diffusion device of aspect 12, wherein the plurality of gas flow channels extend circumferentially about the central axis, and wherein the plurality of liquid flow channels are oriented parallel or substantially parallel to the central axis.

Aspect 14. The microfluidic diffusion device of aspect 12, wherein the plurality of liquid flow channels extend circumferentially about the central axis, and wherein the plurality of gas flow channels are oriented parallel or substantially parallel to the central axis.

Aspect 15. The microfluidic diffusion device of aspect 13, further comprising:
a gas inlet channel extending radially from an outer surface of the patterned membrane toward the cylindrical substrate, wherein the gas inlet channel is positioned in fluid communication with at least a portion of the plurality of gas flow channels; and
a gas outlet channel extending radially from an outer surface of the patterned membrane toward the cylindrical substrate, wherein the gas outlet channel is positioned in fluid communication with at least a portion of the plurality of gas flow channels.

Aspect 16. The microfluidic diffusion device of any one of the preceding aspects, further comprising a housing defining a blood inlet, a blood outlet, a gas inlet, and a gas outlet, wherein the blood inlet and the blood outlet are positioned in fluid communication with at least a portion of the plurality of liquid flow channels, and wherein the gas inlet and the gas outlet are positioned in fluid communication with at least a portion of the plurality of gas flow channels.

Aspect 17. The microfluidic diffusion device of aspect 16, wherein the blood inlet and the blood outlet are oriented in substantial alignment with the central axis, and wherein the gas inlet and the gas outlet are oriented perpendicularly or substantially perpendicularly to the central axis.

Aspect 18. The microfluidic diffusion device of aspect 16, wherein the blood inlet and the blood outlet are oriented perpendicularly or substantially perpendicularly to the central axis, and wherein the gas inlet and the gas outlet are oriented in substantial alignment with the central axis.

Aspect 19. A method comprising:
positioning a source of blood in fluid communication with the plurality of liquid flow channels of the diffusion device of aspect 2;
positioning the plurality of gas flow channels of the artificial lung device in fluid communication with a source of gas,
wherein gas from the source of gas diffuses from the plurality of gas flow channels into blood within the plurality of liquid flow channels.

Aspect 20. The method of aspect 19, wherein the source of blood is a patient.

Aspect 21. The method of aspect 20, wherein the source of gas is air surrounding the diffusion device.

Aspect 22. The method of aspect 20, wherein the source of gas is a container filled with oxygen gas.

Aspect 23. The method of any one of aspects 19-22, further comprising selectively adjusting at least one of a blood flow rate, a gas flow rate, or a composition of the gas provided by the gas source.

Aspect 24. A method of forming a device comprising:
patterning a membrane to define a plurality of flow channels; and
circumferentially rolling the patterned membrane over an outer surface of a cylindrical substrate to define a plurality of concentric membrane layers extending radially outwardly from a central axis of the cylindrical substrate, thereby forming the device,
wherein each flow channel of the plurality of flow channels is configured to receive and permit flow of a fluid.

Aspect 25. The method of aspect 24, wherein at least one membrane layer of the plurality of concentric membrane layers is patterned to define a plurality of gas flow channels that are configured to receive a gas, wherein at least one membrane layer of the plurality of concentric membrane layers is patterned to define a plurality of liquid flow channels that are configured to receive liquid, and wherein the at least one membrane layer permits diffusion of:
(a) gas from the plurality of gas flow channels into the liquid within the plurality of liquid flow channels; or
(b) liquid from the plurality of liquid flow channels into the gas within the plurality of gas flow channels; or
(c) both (a) and (b).

Aspect 26. The method of aspect 25, wherein the plurality of gas flow channels are configured to receive a sweep gas, wherein the plurality of liquid flow channels are configured to receive blood, and wherein the at least one membrane layer permits diffusion of the sweep gas from the plurality of gas flow channels into the blood within the plurality of liquid flow channels.

Aspect 27. The method of aspect 26, wherein the cylindrical substrate and the plurality of concentric membrane layers cooperate to form an artificial lung device.

Aspect 28. The method of any one of aspects 24-27, wherein the patterned membrane comprises a single contiguous sheet of material.

Aspect 29. The method of aspect 28, wherein the patterned membrane comprises a web or film of polydimethylsiloxane (PDMS).

Aspect 30. The method of aspect 28, further comprising unrolling the membrane before patterning of the membrane.

Aspect 31. The method of aspect 28, wherein the membrane is patterned using a laser, and wherein the plurality of flow channels extend inwardly from an exposed surface of the membrane that is patterned by the laser.

Aspect 32. The method of aspect 30, wherein, before patterning of the membrane, the membrane is provided on a source roller with a carrier layer, wherein the source roller is rotated to advance the membrane and the carrier layer in a processing direction, wherein an exposed surface of the membrane is patterned as the membrane and the carrier layer are advanced in the processing direction, wherein a first take-up roller receives the patterned membrane, and wherein a second take-up roller receives the carrier layer after patterning of the membrane.

Aspect 33. The method of aspect 32, further comprising, after patterning of the membrane, applying a surface treatment to the exposed surface of the membrane to activate bonding activity of the membrane.

Aspect 34. The method of aspect 33, wherein the surface treatment comprises plasma, ultraviolet, ozone, corona, or chemical treatment, or combinations thereof.

Aspect 35. The method of any one of aspects 28-34, wherein the patterned membrane has a maximum thickness ranging from about 10 µm to about 250 µm.

Aspect 36. The method of aspect 35, wherein the plurality of gas flow channels are patterned to have a thickness ranging from about 10 µm to about 250 µm.

Aspect 37. The method of aspect 35, wherein the plurality of liquid flow channels are patterned to have a thickness ranging from about 5 µm to about 250 µm.

Aspect 38. The method of any one of aspects 28-37, wherein the plurality of gas flow channels and the plurality of liquid flow channels are engraved in respective portions of the patterned membrane.

Aspect 39. The method of any one of aspects 28-38, wherein at least one membrane layer of the plurality of concentric membrane layers does not comprise gas or liquid flow channels.

Aspect 40. The method of any one of aspects 28-39, wherein the plurality of concentric membrane layers comprise:

a liquid flow layer bonded to the outer surface of the cylindrical substrate and comprising the plurality of liquid flow channels;

a gas flow layer positioned radially outwardly of the liquid flow layer and bonded to the liquid flow layer, wherein the gas flow layer comprises the plurality of gas flow channels; and a capping layer positioned radially outwardly of the gas flow layer and bonded to the gas flow layer to cap the plurality of gas flow channels, wherein the capping layer does not comprise gas or liquid flow channels, and wherein portions of the patterned membrane positioned radially between the plurality of gas flow channels and the plurality of liquid flow channels permit diffusion of gas from the plurality of gas flow channels into the plurality of liquid flow channels.

Aspect 41. The method of aspect 40, wherein the plurality of gas flow channels and the plurality of liquid flow channels are oriented parallel or substantially parallel to the central axis.

Aspect 42. The method of any one of aspects 28-39, wherein the plurality of concentric membrane layers comprises:

a plurality of gas flow layers, each gas flow layer comprising a portion of the plurality of gas flow channels; and a plurality of liquid flow layers, each liquid flow layer comprising a portion of the plurality of liquid flow channels, wherein the gas flow layers and the liquid flow layers are positioned in an alternating pattern moving radially outwardly from the central axis.

Aspect 43. The method of aspect 42, wherein the plurality of gas flow channels extend circumferentially about the central axis, and wherein the plurality of liquid flow channels are oriented parallel or substantially parallel to the central axis.

Aspect 44. The method of aspect 42, wherein the plurality of liquid flow channels extend circumferentially about the central axis, and wherein the plurality of gas flow channels are oriented parallel or substantially parallel to the central axis.

Aspect 45. The method of aspect 43, further comprising:

forming a gas inlet channel extending radially from an outer surface of the patterned membrane toward the cylindrical substrate, wherein the gas inlet channel is positioned in fluid communication with at least a portion of the plurality of gas flow channels; and forming a gas outlet channel extending radially from an outer surface of the patterned membrane toward the cylindrical substrate, wherein the gas outlet channel is positioned in fluid communication with at least a portion of the plurality of gas flow channels.

Aspect 46. The method of any one of aspects 28-45, further comprising positioning the device within a housing, the housing defining a blood inlet, a blood outlet, a gas inlet, and a gas outlet, wherein the blood inlet and the blood outlet are positioned in fluid communication with at least a portion of the plurality of liquid flow channels, and wherein the gas inlet and the gas outlet are positioned in fluid communication with at least a portion of the plurality of gas flow channels.

Aspect 47. The method of aspect 46, wherein the blood inlet and the blood outlet are oriented in substantial alignment with the central axis, and wherein the gas inlet and the gas outlet are oriented perpendicularly or substantially perpendicularly to the central axis.

Aspect 48. The method of aspect 46, wherein the blood inlet and the blood outlet perpendicularly or substantially perpendicularly to the central axis, and wherein the gas inlet and the gas outlet are oriented in substantial alignment with the central axis.

Aspect 49. A three-dimensionally printed microfluidic diffusion device comprising:

a liquid distribution pathway extending along a liquid flow axis and comprising:
at least one liquid inlet;
at least one liquid outlet; and
a capillary bed positioned between the at least one liquid inlet and the at least one liquid outlet relative to the liquid flow axis, the capillary bed comprising a plurality of capillary elements defining respective lumens that are in fluid communication with the at least one liquid inlet and the at least one liquid outlet; and a gas flow pathway extending along a gas flow axis that is perpendicular or substantially perpendicular to the liquid flow axis, wherein the gas flow pathway intersects at least a portion of the capillary bed to define a gas exchange region, and wherein the plurality of capillary elements are formed from a material that permits diffusion of gas from the gas flow pathway into liquid within the plurality of capillary elements.

Aspect 50. The microfluidic diffusion device of aspect 49, wherein the plurality of capillary elements are oriented parallel or substantially parallel to the liquid flow axis.

Aspect 51. The microfluidic diffusion device of aspect 50, wherein the plurality of capillary elements are evenly or substantially evenly distributed within the capillary bed.

Aspect 52. The microfluidic diffusion device of aspect 49, wherein, within the gas exchange region, portions of the gas flow pathway circumferentially surround at least a portion of an outer surface of each capillary element of the plurality of capillary elements.

Aspect 53. The microfluidic diffusion device of aspect 49, wherein the liquid distribution pathway further comprises first and second liquid distribution regions that are respectively positioned between the at least one liquid inlet and the capillary bed and between the capillary bed and the at least one liquid outlet.

Aspect 54. The microfluidic diffusion device of aspect 49, wherein the lumen of each capillary element has an inner diameter ranging from about 10 μm to about 200 μm.

Aspect 55. The microfluidic diffusion device of aspect 49, wherein the plurality of capillary elements comprise photosensitive polydimethylsiloxane (PDMS).

Aspect 56. A method comprising:
using a three-dimensional printer to form the microfluidic diffusion device of aspect 49.

Aspect 57. The method of aspect 56, wherein the three-dimensional printer forms at least the plurality of capillary elements from photosensitive polydimethylsiloxane (PDMS).

Aspect 58. A method comprising:
forming a microfluidic diffusion device having a gas flow pathway and a liquid flow pathway, wherein the microfluidic diffusion device is formed by three-dimensional (3D) printing or by a roll-to-roll process, wherein the gas flow pathway and the liquid flow pathway are separated by a membrane that permits diffusion of gas from the gas flow pathway into the liquid flow pathway, and wherein at least one of the gas flow pathway and the liquid flow pathway has a smallest dimension of less than 250 µm.

Aspect 59. The method of aspect 58, wherein the liquid flow pathway is configured to receive blood, wherein the gas flow pathway is configured to receive a gas comprising oxygen, and wherein the membrane is configured to permit diffusion of oxygen into the liquid flow pathway.

What is claimed is:

1. A three-dimensionally printed diffusion device comprising:
   a liquid distribution pathway extending along a liquid flow axis and comprising:
      at least one liquid inlet;
      at least one liquid outlet; and
      a capillary bed positioned between the at least one liquid inlet and the at least one liquid outlet relative to the liquid flow axis, the capillary bed comprising a plurality of capillary elements defining respective lumens that are in fluid communication with the at least one liquid inlet and the at least one liquid outlet; and
   a gas flow pathway extending along a gas flow axis that is perpendicular or substantially perpendicular to the liquid flow axis,
   wherein the gas flow pathway intersects at least a portion of the capillary bed to define a gas exchange region, and
   wherein the plurality of capillary elements are formed from a material that permits diffusion of gas from the gas flow pathway into liquid within the plurality of capillary elements, and
   wherein, within the gas exchange region, portions of the gas flow pathway circumferentially surround at least a portion of a length of each capillary element of the plurality of capillary elements.

2. The three-dimensionally printed diffusion device of claim 1, wherein the plurality of capillary elements are oriented parallel or substantially parallel to the liquid flow axis.

3. The three-dimensionally printed diffusion device of claim 2, wherein the plurality of capillary elements are evenly or substantially evenly distributed within the capillary bed.

4. The three-dimensionally printed diffusion device of claim 3, wherein the plurality of capillary elements are arranged in a plurality of rows and columns in which a spacing between sequential capillary elements in each column and a spacing between sequential capillary elements in each row is uniform or substantially uniform.

5. The three-dimensionally printed diffusion device of claim 1, wherein the liquid distribution pathway further comprises first and second liquid distribution regions that are respectively positioned between the at least one liquid inlet and the capillary bed and between the capillary bed and the at least one liquid outlet, and wherein the first and second liquid distribution regions comprise a plurality of branches and sub-branches that progressively decrease in inner diameter until reaching the plurality of capillary elements of the capillary bed.

6. The three-dimensionally printed diffusion device of claim 1, wherein the lumen of each capillary element has an inner diameter ranging from 10 µm to about 200 µm.

7. The three-dimensionally printed diffusion device of claim 1, wherein the plurality of capillary elements comprise photosensitive polydimethylsiloxane (PDMS).

8. The three-dimensionally printed diffusion device of claim 1, wherein the gas flow pathway has a gas inlet and a gas outlet positioned on opposing sides of the gas exchange region, wherein the gas flow pathway has a variable width or diameter moving along the gas flow axis, and wherein the width or diameter of the gas flow pathway increases as the gas flow pathway approaches the capillary bed from the gas inlet and the gas outlet.

9. The three-dimensionally printed diffusion device of claim 1, wherein portions of the gas flow pathway circumferentially surround the entire length of each capillary element.

10. The three-dimensionally printed diffusion device of claim 1, wherein the material forming the plurality of capillary elements permits diffusion of gas directly from the gas flow pathway into liquid within the plurality of capillary elements.

11. A method comprising:
    positioning a source of blood in fluid communication with a liquid distribution pathway of a three-dimensionally printed diffusion device, the three-dimensionally printed diffusion device comprising:
       the liquid distribution pathway extending along a liquid flow axis and comprising:
          at least one liquid inlet;
          at least one liquid outlet; and
          a capillary bed positioned between the at least one liquid inlet and the at least one liquid outlet relative to the liquid flow axis, the capillary bed comprising a plurality of capillary elements defining respective lumens that are in fluid communication with the at least one liquid inlet and the at least one liquid outlet; and
       a gas flow pathway extending along a gas flow axis that is perpendicular or substantially perpendicular to the liquid flow axis,
       wherein the gas flow pathway intersects at least a portion of the capillary bed to define a gas exchange region, and
       wherein the plurality of capillary elements are formed from a material that permits diffusion of gas from the gas flow pathway into liquid within the plurality of capillary elements, and
       wherein, within the gas exchange region, portions of the gas flow pathway circumferentially surround at least a portion of a length of each capillary element of the plurality of capillary elements;
    positioning the gas flow pathway of the diffusion device in fluid communication with a source of gas,
    wherein gas from the source of gas diffuses from the gas flow pathway into blood within the plurality of capillary element.

12. The method of claim 11, wherein the source of blood is a patient.

13. The method of claim 12, wherein the source of gas is air surrounding the diffusion device.

14. The method of claim 12, wherein the source of gas is a container filled with oxygen gas.

15. A method comprising:
    printing a diffusion device with a three-dimensional (3D) printer, the diffusion device comprising:
       a liquid distribution pathway extending along a liquid flow axis and comprising:
          at least one liquid inlet;
          at least one liquid outlet; and
          a capillary bed positioned between the at least one liquid inlet and the at least one liquid outlet relative to the liquid flow axis, the capillary bed comprising a plurality of capillary elements defining respective lumens that are in fluid communication with the at least one liquid inlet and the at least one liquid outlet; and a gas flow pathway extending along a gas flow axis that is perpendicular or substantially perpendicular to the liquid flow axis, wherein the gas flow pathway intersects at least a portion of the capillary bed to define a gas exchange region, and wherein the plurality of capillary elements are formed from a material that permits diffusion of gas from the gas flow pathway into liquid within the plurality of capillary elements, and wherein, within the gas exchange region, portions of the gas flow pathway circumferentially surround at least a portion of a length of each capillary element of the plurality of capillary elements.

16. The method of claim 15, wherein at least one of the gas flow pathway and the liquid flow pathway has a smallest dimension of less than 250 µm.

17. The method of claim 15, wherein the liquid flow pathway is configured to receive blood, wherein the gas flow pathway is configured to receive a gas comprising oxygen, and wherein the material is configured to permit diffusion of oxygen into the liquid flow pathway.

18. The method of claim 15, wherein the three-dimensional printer forms at least the plurality of capillary elements from photosensitive polydimethylsiloxane (PDMS).

19. The method of claim 15, wherein the plurality of capillary elements are oriented parallel or substantially parallel to the liquid flow axis.

20. The method of claim 15, wherein the plurality of capillary elements are evenly or substantially evenly distributed within the capillary bed.

* * * * *